United States Patent
Suzuki et al.

(10) Patent No.: US 10,526,603 B1
(45) Date of Patent: Jan. 7, 2020

(54) DOUBLE-STRANDED RIBONUCLEIC ACID CAPABLE OF SUPPRESSING EXPRESSION OF COMPLEMENT C5

(71) Applicant: Eisai R&D Management Co., Ltd., Bunkyo-ku, Tokyo (JP)

(72) Inventors: Yuta Suzuki, Tsukuba (JP); Sotaro Motoi, Kobe (JP); Yoshinori Takahashi, Tsukuba (JP); Kazuhiro Tahara, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/354,916

(22) Filed: Mar. 15, 2019

(30) Foreign Application Priority Data

Oct. 26, 2018 (JP) .................................. 2018-201777

(51) Int. Cl.
*C12N 15/113* (2010.01)
*A61P 7/00* (2006.01)

(52) U.S. Cl.
CPC .............. *C12N 15/113* (2013.01); *A61P 7/00* (2018.01); *C12N 2310/111* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

2016/0237438 A1   8/2016   Brown et al.

FOREIGN PATENT DOCUMENTS

| WO | WO 2014/160129 | 10/2014 |
| WO | WO 2016/044419 | 3/2016 |
| WO | WO 2016/201301 | 12/2016 |

OTHER PUBLICATIONS

Hillmen et al., "Effect of eculizumab on hemolysis and transfusion requirements in patients with paroxysmal nocturnal hemoglobinuria," New England Journal of Medicine, 2004, 350(6):552-559.

Howard et al., "A randomized, double-blind, placebo-controlled phase II study of eculizumab in patients with refractory generalized myasthenia gravis," Muscle Nerve, 2013, 48(1):76-84.

Legendre et al., "Terminal complement inhibitor eculizumab in atypical hemolytic-uremic syndrome," New England Journal of Medicine, 2013, 368(23):2169-2181.

Pittock et al., "Eculizumab in AQP4-IgG-positive relapsing neuromyelitis optica spectrum disorders: an open-label pilot study," The Lancet Neurology, 2013, 12(6):554-562.

Stegall et al., "Terminal complement inhibition decreases antibody-mediated rejection in sensitized renal transplant recipients," American Journal of Transplantation, 2011, 11(11):2405-2413.

*Primary Examiner* — Jennifer Pitrak McDonald
(74) *Attorney, Agent, or Firm* — Fish & Richardson P.C.

(57) ABSTRACT

Provided is a novel double-stranded ribonucleic acid for suppressing expression of complement C5. A double-stranded ribonucleic acid comprising a combination of sense strand and antisense strand, wherein the combination of the sense strand and antisense strand are selected from the group consisting of combinations: SEQ ID NO: 13/14, SEQ ID NO: 159/160, SEQ ID NO: 115/116, SEQ ID NO: 117/118, SEQ ID NO: 119/120, SEQ ID NO: 121/122, SEQ ID NO: 123/124, SEQ ID NO: 125/126, SEQ ID NO: 127/128, SEQ ID NO: 129/130, SEQ ID NO: 131/132, SEQ ID NO: 133/134, SEQ ID NO: 137/138, SEQ ID NO: 139/140, SEQ ID NO: 141/142, SEQ ID NO: 143/144, SEQ ID NO: 145/146, SEQ ID NO: 147/148, SEQ ID NO: 149/150, SEQ ID NO: 151/152, and SEQ ID NO: 153/154.

20 Claims, 6 Drawing Sheets

Specification includes a Sequence Listing.

DOUBLE-STRANDED RIBONUCLEIC ACID CAPABLE OF SUPPRESSING EXPRESSION OF COMPLEMENT C5

CROSS-REFERENCE TO RELATED APPLICATION

This application claims the benefit of Japanese patent application No. 2018-201777 filed on Oct. 26, 2018, the disclosure of which is herein incorporated by reference in its entirety.

TECHNICAL FIELD

The present invention relates to a double-stranded ribonucleic acid (dsRNA) capable of suppressing expression of complement C5. In particular, the present invention relates to a double-stranded ribonucleic acid, a lipid complex encapsulating the double-stranded ribonucleic acid, and a complement C5 inhibitor and pharmaceutical composition comprising the double-stranded ribonucleic acid or the lipid complex.

BACKGROUND

A protein group called complement includes proteins indicated as C1 to C9, and these proteins are successively activated through three different pathways (classical pathway, lectin pathway, alternative pathway) to elicit immune response. The fifth complement component, C5, is cleaved to C5a and C5b by C5 convertase. C5a is called anaphylatoxin, and induces inflammatory response for various cells via C5aR (CD88) and C5L2 (GPR77). C5b sequentially reacts with C6 to C9 to be converted into a membrane attack complex (MAC) as a final product, which causes bacteriolysis to pathogens or cell lysis. The complement system may elicit strong cytotoxicity to host cells if the complement system fails to be suitably controlled or is excessively activated.

From previous studies, the complement C5 is known to be associated with various diseases including paroxysmal nocturnal hemoglobinuria (PNH), atypical hemolytic uremic syndrome (aHUS), myasthenia gravis (MG), neuromyelitis optica (NMO), antibody-mediated rejection in kidney transplantation, Guillain-Barre syndrome, antineutrophil cytoplasmic antibody-associated vasculitis (ANCA-associated vasculitis), amyotrophic lateral sclerosis (ALS), Parkinson's disease (PD), autoimmune encephalitis, IgG4-related diseases, asthma, antiphospholipid antibody syndrome, ischemia-reperfusion injury, typical hemolytic uremic syndrome (tHUS), multifocal motor neuropathy (MMN), multiple sclerosis (MS), thrombotic thrombocytopenic purpura (TTP), spontaneous abortion, habitual abortion, traumatic brain injury, cold agglutinin disease, dermatomyositis, hemolytic uremic syndrome associated with Shigatoxin-producing *Escherichia coli* (*E. coli*), graft dysfunction, myocardial infarction, sepsis, atherosclerosis, septic shock, spinal cord injury, psoriasis, autoimmune hemolytic anemia (AIHA), antiphospholipid syndrome (APS), myocarditis, immune complex vasculitis, Takayasu's disease, and Kawasaki's disease (arteritis). Thus, inhibition or suppression of expression of complement C5 is expected to lead to successful treatment of these diseases. In particular, inhibition of complement C5 is suggested to be effective for treating or preventing paroxysmal nocturnal hemoglobinuria (Non Patent Literature 1), atypical hemolytic uremic syndrome (Non Patent Literature 2), myasthenia gravis (Non Patent Literature 3), neuromyelitis optica (Non Patent Literature 4), and antibody-mediated kidney transplant rejections (Non Patent Literature 5).

The anti-C5 monoclonal antibody eculizumab (Soliris (registered trademark)) exhibits high affinity for complement C5, and suppresses excessive activation of the complement through inhibition of cleavage of C5 into C5a/C5b and accompanying formation of a membrane attack complex. Thereby, eculizumab exhibits inhibitory effect on hemolysis, and thus is known as a therapeutic agent for paroxysmal nocturnal hemoglobinuria and atypical hemolytic uremic syndrome. In addition, eculizumab is known as a therapeutic agent for generalized myasthenia gravis (gMG). However, eculizumab is very expensive, and hence development of alternative means applicable to treatment and prevention of complement C5-mediated diseases is desired.

Examples of methods for suppressing expression of complement C5 include methods utilizing RNA interference (hereinafter, also referred to as "RNAi"). For example, a double-stranded ribonucleic acid (dsRNA) agent is known, which induces cleavage of an RNA transcript of the C5 gene via an RNA-induced silencing complex (RISC) (Patent Literature 1).

CITATION LIST

Patent Literature

[Patent Literature 1] WO 2014/160129

Non-Patent Literature

[Non-Patent Literature 1] Non Patent Literature 1: Peter Hillmen et al., The New England Journal of Medicine 2004 Feb. 5; 350(6): 552-559.
[Non-Patent Literature 2] Legendre C M et al., The New England Journal of Medicine 2013 Jun. 6; 368(23): 2169-2181.
[Non-Patent Literature 3] Howard J F Jr et al., Muscle Nerve 2013 July; 48(1): 76-84.
[Non-Patent Literature 4] Pittock S J et al., The Lancet Neurology 2013 June; 12(6): 554-562.
[Non-Patent Literature 5] Stegall M D et al., American Journal of Transplantation 2011 November; 11(11): 2405-2413.

SUMMARY

An object of the present invention is to provide a novel double-stranded ribonucleic acid for suppressing expression of complement C5.

The present invention provides, for example, the following <1> to <36>.
<1> A double-stranded ribonucleic acid comprising:
 a combination of a sense strand and an antisense strand,
 wherein the combination of the sense strand and the antisense strand are selected from the group consisting of combinations:
 SEQ ID NO: 13 and SEQ ID NO: 14; SEQ ID NO: 159 and SEQ ID NO: 160; SEQ ID NO: 115 and SEQ ID NO: 116; SEQ ID NO: 117 and SEQ ID NO: 118; SEQ ID NO: 119 and SEQ ID NO: 120; SEQ ID NO: 121 and SEQ ID NO: 122; SEQ ID NO: 123 and SEQ ID NO: 124; SEQ ID NO: 125 and SEQ ID NO: 126; SEQ ID NO: 127 and SEQ ID NO: 128; SEQ ID NO: 129 and SEQ ID NO: 130; SEQ ID NO: 131 and SEQ ID NO: 132; SEQ ID NO: 133 and SEQ ID NO: 134; SEQ ID NO: 137 and SEQ ID NO: 138, SEQ ID NO: 139 and SEQ ID NO: 140; SEQ ID NO: 141 and SEQ ID NO: 142; SEQ ID NO: 143 and SEQ ID NO: 144; SEQ ID NO: 145 and SEQ ID NO: 146; SEQ ID NO: 147 and SEQ ID NO: 148; SEQ ID NO: 149 and SEQ ID NO: 150; SEQ ID NO: 151 and SEQ ID NO: 152; and SEQ ID NO: 153 and SEQ ID NO: 154.

<2> A double-stranded ribonucleic acid comprising:
a combination of a sense strand and an antisense strand, wherein the combination of the sense strand and the antisense strand are selected from the group consisting of combinations:
SEQ ID NO: 159 and SEQ ID NO: 160; SEQ ID NO: 139 and SEQ ID NO: 140; SEQ ID NO: 141 and SEQ ID NO: 142; SEQ ID NO: 143 and SEQ ID NO: 144; SEQ ID NO: 145 and SEQ ID NO: 146; SEQ ID NO: 147 and SEQ ID NO: 148; and SEQ ID NO: 153 and SEQ ID NO: 154.

<3> A double-stranded ribonucleic acid comprising:
a combination of a sense strand and an antisense strand, wherein the combination of the sense strand and the antisense strand are selected from the group consisting of combinations:
SEQ ID NO: 159 and SEQ ID NO: 160; SEQ ID NO: 141 and SEQ ID NO: 142; SEQ ID NO: 143 and SEQ ID NO: 144; SEQ ID NO: 145 and SEQ ID NO: 146; SEQ ID NO: 147 and SEQ ID NO: 148; and SEQ ID NO: 153 and SEQ ID NO: 154.

<4> A double-stranded ribonucleic acid comprising:
a combination of a sense strand and an antisense strand, wherein the combination of the sense strand and the antisense strand are selected from the group consisting of combinations:
SEQ ID NO: 141 and SEQ ID NO: 142; SEQ ID NO: 143 and SEQ ID NO: 144; SEQ ID NO: 145 and SEQ ID NO: 146; SEQ ID NO: 147 and SEQ ID NO: 148; and SEQ ID NO: 153 and SEQ ID NO: 154.

<5> A double-stranded ribonucleic acid comprising:
a sense strand of SEQ ID NO: 141; and
an antisense strand of SEQ ID NO: 142.

<6> A double-stranded ribonucleic acid comprising:
a sense strand of SEQ ID NO: 143; and
an antisense strand of SEQ ID NO: 144.

<7> A double-stranded ribonucleic acid comprising:
a sense strand of SEQ ID NO: 145; and
an antisense strand of SEQ ID NO: 146.

<8> A double-stranded ribonucleic acid comprising:
a sense strand of SEQ ID NO: 147; and
an antisense strand of SEQ ID NO: 148.

<9> A double-stranded ribonucleic acid comprising:
a sense strand of SEQ ID NO: 153; and
an antisense strand of SEQ ID NO: 154.

<10> A double-stranded ribonucleic acid comprising:
a sense strand of SEQ ID NO: 159; and
an antisense strand of SEQ ID NO: 160.

<11> A complement C5 inhibitor comprising:
the double-stranded ribonucleic acid according to any one of <1> to <10>.

<12> A pharmaceutical composition comprising:
the double-stranded ribonucleic acid according to any one of <1> to <10>.

<13> The pharmaceutical composition according to <12>, further comprising a pharmaceutically acceptable carrier.

<14> The pharmaceutical composition according to <12> or <13>, for use in treating paroxysmal nocturnal hemoglobinuria.

<15> The pharmaceutical composition according to <12> or <13>, for use in treating atypical hemolytic uremic syndrome.

<16> A lipid complex encapsulating the double-stranded ribonucleic acid according to any one of <1> to <10>.

<17> The lipid complex according to <16>, comprising:
a cationic lipid; and
at least one lipid selected from the group consisting of neutral lipid, polyethylene glycol-modified lipid, and sterol.

<18> The lipid complex according to <17>, wherein the cationic lipid is 2-{9-oxo-9-[(3-pentyloctyl)oxy]nonyl}dodecyl 1-methylpiperidine-4-carboxylate.

<19> The lipid complex according to <17>, wherein the neutral lipid is distearoylphosphatidylcholine (DSPC).

<20> The lipid complex according to <17>, wherein the polyethylene glycol-modified lipid is MPEG2000-DMG (MPEG2000-dimyristyl glycerol).

<21> The lipid complex according to <17>, wherein the sterol is cholesterol.

<22> A complement C5 inhibitor comprising:
the lipid complex according to any one of <16> to <21>.

<23> A pharmaceutical composition comprising:
the lipid complex according to any one of <16> to <21>.

<24> The pharmaceutical composition according to <23>, further comprising a pharmaceutically acceptable carrier.

<25> The pharmaceutical composition according to <23> or <24>, for use in treating paroxysmal nocturnal hemoglobinuria.

<26> The pharmaceutical composition according to <23> or <24>, for use in treating atypical hemolytic uremic syndrome.

<27> A method for treating paroxysmal nocturnal hemoglobinuria, comprising:
administering the double-stranded ribonucleic acid according to any one of <1> to <10> to a patient in need thereof.

<28> A method for treating atypical hemolytic uremic syndrome, comprising:
administering the double-stranded ribonucleic acid according to any one of <1> to <10> to a patient in need thereof.

<29> The double-stranded ribonucleic acid according to any one of <1> to <10>, for use in treating paroxysmal nocturnal hemoglobinuria.

<30> The double-stranded ribonucleic acid according to any one of <1> to <10>, for use in treating atypical hemolytic uremic syndrome.

<31> Use of the double-stranded ribonucleic acid according to any one of <1> to <10>, in the manufacture of a pharmaceutical composition for treating paroxysmal nocturnal hemoglobinuria.

<32> Use of the double-stranded ribonucleic acid according to any one of <1> to <10>, in the manufacture of a pharmaceutical composition for treating atypical hemolytic uremic syndrome.

<33> A method for treating paroxysmal nocturnal hemoglobinuria, comprising:
administering the lipid complex according to any one of <16> to <21> to a patient in need thereof.

<34> A method for treating atypical hemolytic uremic syndrome, comprising: administering the lipid complex according to any one of <16> to <21> to a patient in need thereof.

<35> The lipid complex according to any one of <16> to <21>, for use in treating paroxysmal nocturnal hemoglobinuria.

<36> The lipid complex according to any one of <16> to <21>, for use in treating atypical hemolytic uremic syndrome.

<37> Use of the lipid complex according to any one of <16> to <21>, in the manufacture of a pharmaceutical composition for treating paroxysmal nocturnal hemoglobinuria.
<38> Use of the lipid complex according to any one of <16> to <21>, in the manufacture of a pharmaceutical composition for treating atypical hemolytic uremic syndrome.

In accordance with the present invention, a novel double-stranded ribonucleic acid capable of suppressing expression of complement C5, a lipid complex encapsulating the nucleic acid in the lipid complex, and a complement C5 inhibitor and pharmaceutical composition comprising the nucleic acid or the lipid complex can be provided.

The double-stranded ribonucleic acid according to the present invention can suppress expression of complement C5 to suppress hemolysis, and hence can be applicable as a therapeutic agent for paroxysmal nocturnal hemoglobinuria (PNH) and atypical hemolytic uremic syndrome (aHUS).

DETAILED DESCRIPTION

Figure 1:
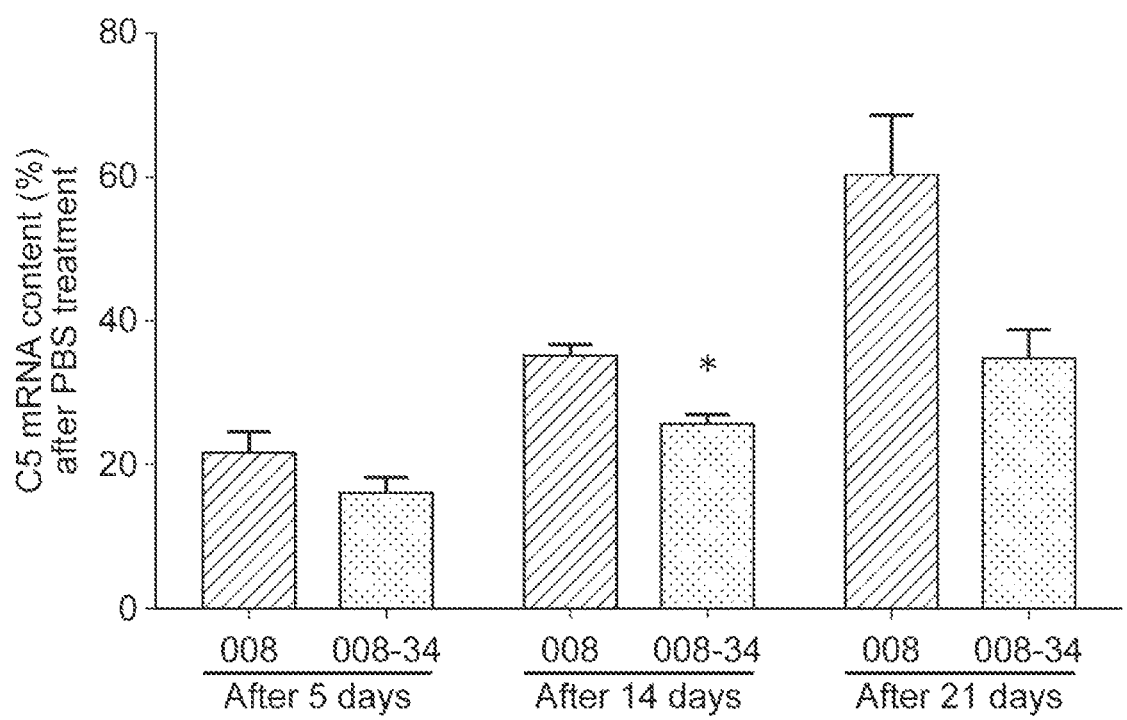
FIG. 1 shows graphs representing results of liver C5 mRNA residual rates after administration of siRNA-008 and liver C5 mRNA residual rates after administration of siRNA-008-34 in Example 5.

Examples of genes encoding complement C5 targeted by the double-stranded ribonucleic acid according to an embodiment include, but are not limited to, C5 derived from humans, mice, and monkeys. Information on C5 gene sequences is available from public databases including registered sequence information such as GenBank provided by The National Center for Biotechnology Information (NCBI), or can be obtained by designing a primer based on information of a nucleotide sequence for C5 from a closely related animal species followed by cloning therewith from an RNA extracted from a desired animal species. Examples of the sequence of an mRNA transcript corresponding to the target gene human C5 include the sequence of a human C5 mRNA transcript registered as GenBank Accession No. NM_001735.2 (GI: 38016946). The term "C5 gene" herein is not limited to a gene having a particular sequence. For example, naturally-occurring C5 genes with single nucleotide polymorphism can be also included in the term.

In a double-stranded ribonucleic acid according to an embodiment comprising a sense strand and an antisense strand, combination of sense strand/antisense strand is selected from the group consisting of: SEQ ID NO: 13/SEQ ID NO: 14, SEQ ID NO: 159/SEQ ID NO: 160, SEQ ID NO: 115/SEQ ID NO: 116, SEQ ID NO: 117/SEQ ID NO: 118, SEQ ID NO: 119/SEQ ID NO: 120, SEQ ID NO: 121/SEQ ID NO: 122, SEQ ID NO: 123/SEQ ID NO: 124, SEQ ID NO: 125/SEQ ID NO: 126, SEQ ID NO: 127/SEQ ID NO: 128, SEQ ID NO: 129/SEQ ID NO: 130, SEQ ID NO: 131/SEQ ID NO: 132, SEQ ID NO: 133/SEQ ID NO: 134, SEQ ID NO: 137/SEQ ID NO: 138, SEQ ID NO: 139/SEQ ID NO: 140, SEQ ID NO: 141/SEQ ID NO: 142, SEQ ID NO: 143/SEQ ID NO: 144, SEQ ID NO: 145/SEQ ID NO: 146, SEQ ID NO: 147/SEQ ID NO: 148, SEQ ID NO: 149/SEQ ID NO: 150, SEQ ID NO: 151/SEQ ID NO: 152, and SEQ ID NO: 153/SEQ ID NO: 154. The combinations respectively correspond to the sequences of siRNA-008, siRNA-008-01, siRNA-008-02, siRNA-008-08, siRNA-008-09, siRNA-008-10, siRNA-008-11, siRNA-008-12, siRNA-008-13, siRNA-008-14, siRNA-008-22, siRNA-008-23, siRNA-008-30, siRNA-008-31, siRNA-008-32, siRNA-008-33, siRNA-008-34, siRNA-008-35, siRNA-008-36, siRNA-008-37, and siRNA-008-38 in the present specification.

In the double-stranded ribonucleic acid according to the embodiment, a sense strand and an antisense strand as any one of the combinations (1) to (21) are pairing.

(1) a sense strand of SEQ ID NO: 13, and an antisense strand of SEQ ID NO: 14
(2) a sense strand of SEQ ID NO: 159, and an antisense strand of SEQ ID NO: 160
(3) a sense strand of SEQ ID NO: 115, and an antisense strand of SEQ ID NO: 116
(4) a sense strand of SEQ ID NO: 117, and an antisense strand of SEQ ID NO: 118
(5) a sense strand of SEQ ID NO: 119, and an antisense strand of SEQ ID NO: 120
(6) a sense strand of SEQ ID NO: 121, and an antisense strand of SEQ ID NO: 122
(7) a sense strand of SEQ ID NO: 123, and an antisense strand of SEQ ID NO: 124
(8) a sense strand of SEQ ID NO: 125, and an antisense strand of SEQ ID NO: 126
(9) a sense strand of SEQ ID NO: 127, and an antisense strand of SEQ ID NO: 128
(10) a sense strand of SEQ ID NO: 129, and an antisense strand of SEQ ID NO: 130
(11) a sense strand of SEQ ID NO: 131, and an antisense strand of SEQ ID NO: 132
(12) a sense strand of SEQ ID NO: 133, and an antisense strand of SEQ ID NO: 134
(13) a sense strand of SEQ ID NO: 137, and an antisense strand of SEQ ID NO: 138
(14) a sense strand of SEQ ID NO: 139, and an antisense strand of SEQ ID NO: 140
(15) a sense strand of SEQ ID NO: 141, and an antisense strand of SEQ ID NO: 142
(16) a sense strand of SEQ ID NO: 143, and an antisense strand of SEQ ID NO: 144
(17) a sense strand of SEQ ID NO: 145, and an antisense strand of SEQ ID NO: 146
(18) a sense strand of SEQ ID NO: 147, and an antisense strand of SEQ ID NO: 148
(19) a sense strand of SEQ ID NO: 149, and an antisense strand of SEQ ID NO: 150
(20) a sense strand of SEQ ID NO: 151, and an antisense strand of SEQ ID NO: 152
(21) a sense strand of SEQ ID NO: 153, and an antisense strand of SEQ ID NO: 154

Each of the combinations (1) to (21) of a sense strand and an antisense strand includes a region complementary to each other. For example, a double-stranded ribonucleic acid including the combination (1) of the sense strand of SEQ ID NO: 13 and the antisense strand of SEQ ID NO: 14 includes the following complementary strands (dT^dT at the 3'-terminal is not shown, see Table 1 for more details).

5'-uGGuAuAuGuGuuGcuGAu-3' (SEQ ID NO: 13)
3'-AcCAuAuAcAcAAcGAcUA-5' (SEQ ID NO: 14)

In a double-stranded ribonucleic acid according to an embodiment comprising a sense strand and an antisense strand, combination of sense strand/antisense strand is selected from the group consisting of: SEQ ID NO: 159/SEQ ID NO: 160, SEQ ID NO: 139/SEQ ID NO: 140, SEQ ID NO: 141/SEQ ID NO: 142, SEQ ID NO: 143/SEQ ID NO: 144, SEQ ID NO: 145/SEQ ID NO: 146, SEQ ID NO: 147/SEQ ID NO: 148, and SEQ ID NO: 153/SEQ ID NO: 154. The combinations respectively correspond to the sequences of siRNA-008-01, siRNA-008-31, siRNA-008-32, siRNA-008-33, siRNA-008-34, siRNA-008-35, and siRNA-008-38 in the present specification.

In a double-stranded ribonucleic acid according to an embodiment comprising a sense strand and an antisense strand, combination of sense strand/antisense strand is selected from the group consisting of: SEQ ID NO: 141/SEQ ID NO: 142, SEQ ID NO: 143/SEQ ID NO: 144, SEQ ID NO: 145/SEQ ID NO: 146, SEQ ID NO: 147/SEQ ID NO: 148, and SEQ ID NO: 153/SEQ ID NO: 154. The combinations respectively correspond to the sequences of siRNA-008-32, siRNA-008-33, siRNA-008-34, siRNA-008-35, and siRNA-008-38 in the present specification.

A double-stranded ribonucleic acid according to an embodiment comprising a sense strand and an antisense strand includes a sense strand of SEQ ID NO: 141 and an antisense strand of SEQ ID NO: 142. The combination corresponds to the sequence of siRNA-008-32 in the present specification.

A double-stranded ribonucleic acid according to an embodiment comprising a sense strand and an antisense strand includes a sense strand of SEQ ID NO: 143 and an antisense strand of SEQ ID NO: 144. The combination corresponds to the sequence of siRNA-008-33 in the present specification.

A double-stranded ribonucleic acid according to an embodiment comprising a sense strand and an antisense strand includes a sense strand of SEQ ID NO: 145 and an antisense strand of SEQ ID NO: 146. The combination corresponds to the sequence of siRNA-008-34 in the present specification.

A double-stranded ribonucleic acid according to an embodiment comprising a sense strand and an antisense strand includes a sense strand of SEQ ID NO: 147 and an antisense strand of SEQ ID NO: 148. The combination corresponds to the sequence of siRNA-008-35 in the present specification.

A double-stranded ribonucleic acid according to an embodiment comprising a sense strand and an antisense strand includes a sense strand of SEQ ID NO: 153 and an antisense strand of SEQ ID NO: 154. The combination corresponds to the sequence of siRNA-008-38 in the present specification.

The antisense strand according to an embodiment is substantially complementary to at least a part of an mRNA transcript of a C5 gene. Here, the phrase "substantially complementary" includes not only cases that the antisense strand is completely complement to a part of an mRNA transcript of a C5 gene but also cases that there are one to several acceptable mismatches between the antisense strand and a part of an mRNA transcript of C5 gene.

The sense strand according to an embodiment is substantially complementary to at least a part of the nucleotide sequence of the antisense strand. The phrase "substantially complementary" includes not only cases that the sense strand is completely complement to a part of the nucleotide sequence of the antisense strand but also cases that there are one to several acceptable mismatches between the sense strand and a part of the nucleotide sequence of the antisense strand. The phrase "completely complementary" may apply not only to cases that lengths of the sense strand and antisense strand are the same and they are completely complementary, but also to cases when the oligonucleotide of the longer of the sense strand and the antisense strand includes a nucleotide sequence completely complementary to the oligonucleotide of the shorter.

The double-stranded ribonucleic acid according to an embodiment also includes a modified nucleotide, as described later (see also Table 1). Hence, the term "nucleotide" used herein is intended not only to refer to guanosine-3'-phosphate, cytidine-3'-phosphate, adenosine-3'-phosphate, and uridine-3'-phosphate, but also to encompass various modified nucleotides.

The term "double-stranded ribonucleic acid" or "dsRNA" herein refers to a ribonucleic acid (RNA) molecule having double-stranded structure including two antiparallel, substantially complementary oligonucleotides, or a complex thereof. Examples of double-stranded ribonucleic acids herein include, but are not limited to, siRNAs (small interfering RNAs). The double-stranded ribonucleic acid according to an embodiment comprises a sense strand and an antisense strand. Through RNAi using the double-stranded ribonucleic acid according to an embodiment, an mRNA for a C5 gene is cleaved as the target mRNA molecule in an RISC complex, and as a result expression of C5 is suppressed. For example, expression of C5 in cells in a subject is suppressed.

The double-stranded ribonucleic acid according to an embodiment can be synthesized, for example, by using a method with chemical synthesis known in the art (e.g., described in Nucleic Acid Research, 35(10), 3287-96 (2007)) and enzymatic transcription.

The double-stranded ribonucleic acid according to an embodiment includes various modifications. Modification can be performed by using a method known in the art. Examples of the modification include sugar modification.

Examples of the sugar modification include modification for the ribose moiety constituting ribonucleoside, specifically, substitution or addition at the hydroxy group at the 2'-position, more specifically, 2'-O-methyl-modified nucleotide in which the hydroxy group has been substituted with a methoxy group. Nucleotides represented as lowercase a, u, g, and c in Table 1 are 2'-O-methyl-modified nucleotides, and the sense strand and antisense strand of the double-stranded ribonucleic acid according to an embodiment each include 2'-O-methyl-modified nucleotide.

The double-stranded ribonucleic acid can be modified by inserting an additional nucleotide or nucleotide derivative, which is called overhang, into the 3'-side or 5'-side of a region where the sense strand and the antisense strand are forming a double strand. The double-stranded ribonucleic acid according to an embodiment includes the sense strand and/or the antisense strand including deoxy-thymidine (dT) at the 3'-terminal as SEQ ID NO: 13/SEQ ID NO: 14, and the sense strand and/or the antisense strand including inverted deoxy-thymidine (idT) as SEQ ID NO: 129. The double-stranded ribonucleic acid according to an embodiment also includes the sense strand and/or the antisense strand including U, A, and so forth, added as an overhang sequence, for example, that including UUUU added at the 3'-terminal of the antisense strand as SEQ ID NOs: 140 and 142.

Alternatively, the double-stranded ribonucleic acid can be backbone-modified through modification or substitution of the phosphodiester bond. Examples of the modification or substitution of the phosphodiester bond include a phosphorothioate bond. The double-stranded ribonucleic acid according to an embodiment also includes that including neighboring nucleotides connected with a phosphorothioate bond as SEQ ID NO: 13, SEQ ID NO: 14, and SEQ ID NO: 121.

The double-stranded ribonucleic acid according to an embodiment can be introduced into cells in a subject by using a chemical method (e.g., transfection), physical method (e.g., electroporation, microinjection), or biological method (e.g., virus vectors) known in the art.

Transfection is a method of bonding a nucleic acid to a positively charged substance (such as a liposome and polymer) to form a complex followed by allowing cells to incorporate the complex by endocytosis through attracting the complex to negatively charged cell surfaces. Transfection can be performed by using a known method, and can be performed by using a commercially available transfection reagent (e.g., TransIT (registered trademark) series from Takara Bio Inc., Lipofectamine (registered trademark) series from Invitrogen) in a simple manner.

Nucleic acid molecules are easily degraded by ribonuclease present in the living body and each nucleic acid molecule itself is a negatively charged polymer, and hence it is difficult for nucleic acid molecules to pass cell membranes, which are also negatively charged. As an effective method for delivering nucleic acid molecules having such character to the cytoplasm, a technique with a Drug Delivery System (DDS) using a lipid complex, polymer, or the like has been developed.

(Lipid Complex)

In some embodiments, a lipid complex comprising: (I) the double-stranded ribonucleic acid, (II) a cationic lipid, and (III) at least one lipid selected from the group consisting of neutral lipid, polyethylene glycol-modified lipid (PEG lipid), and sterol, is provided. Examples of the lipid complex herein include, but are not limited to, LNPs (lipid nanoparticles).

Examples of the form of a complex formed of a lipid containing a cationic lipid and the double-stranded ribonucleic acid include a complex of the double-stranded ribonucleic acid and a membrane consisting of a lipid monolayer (single molecule) (reverse micelle); a complex of the double-stranded ribonucleic acid and a liposome; and a complex of the double-stranded ribonucleic acid and a micelle. In a lipid complex according to an embodiment of the present invention, the double-stranded ribonucleic acid is encapsulated in a fine particle comprising a lipid containing a cationic lipid.

The lipid complex according to an embodiment contains the double-stranded ribonucleic acid in a content of for example, 0.01 to 50% by weight, 0.1 to 30% by weight, or 1 to 10% by weight to the total weight of the lipid complex.

Cationic lipid is an amphiphilic molecule having a lipophilic region including one or more hydrocarbon groups and a hydrophilic region including a polar group to be protonated at specific pH. Examples of the cationic lipid according to an embodiment include, but are not particularly limited to, cationic lipids described in International Publication Nos. WO 2015/105131, WO 2016/104580, and WO 2017/222016, and alternatively a cationic lipid with improved biodegradability described in International Publication No. WO 2016/104580 or WO 2017/222016 can be used. Examples of the cationic lipid according to an embodiment include 1-oxo-1-(undecan-5-yloxy)nonadecan-10-yl-1-methylpiperidine-4-carboxylate, 1-((2-butyloctyl)oxy)-1-oxononadecan-10-yl-1-methylpiperidine-4-carboxylate, 1-oxo-1-(undecan-5-yloxy)heptadecan-8-yl-1-methylpiperidine 4-carboxylate, 21-oxo-21-(undecan-5-yloxy)heneicosan-10-yl-1-methylpiperidine4-carboxylate, 21-(octan-3-yloxy)-21-oxoheneicosan-10-yl-1-methylpiperidine-4-carboxylate, 1-((2-butyloctyl)oxy)-1-oxoicosan-10-yl-1-methylpiperidine-4-carboxylate, (Z)-1-((2-butylnon-3-en-1-yl)oxy)-1-oxoicosan-10-yl-1-methylpiperidine-4-carboxylate, 1-oxo-1-((3-pentyloctyl)oxy)icosan-10-yl-1-methylpiperidine-4-carboxylate, 1-((3,4-dipropylheptyl)oxy)-1-oxoicosan-10-yl-1-methylpiperidine-4-carboxylate, 1-((6-(butyldisulfanyl)-3-(3-(butyldisulfanyl)propyl)hexyl)oxy)-1-oxoicosan-10-yl-1-methylpiperidine-4-carboxylate, 2-butyloctyl-10-((4-(dimethylamino)butanoyl)oxy)icosanoate, 2-{9-[(2-butyloctyl)oxy]-9-oxononyl}dodecyl 1-methylpiperidine-4-carboxylate, 2-(9-oxo-9-[(3-pentyloctyl)oxy]nonyl) dodecyl 1-methylpiperidine-4-carboxylate, 2-nonyl-11-oxo-11-[(3-pentyloctyl)oxy]undecyl 1-methylpiperidine-4-carboxylate, bis(3-pentyloctyl) 9-{[(1-methylpiperidine-4-carbonyl)oxy]methyl} heptadecanedioate, and di[(Z)-2-nonen-1-yl] 9-{[(1-methylpiperidine-4-carbonyl)oxy]methyl} heptadecanedioate. In an embodiment, the cationic lipid is 2-{9-oxo-9-[(3-pentyloctyl)oxy]nonyl}dodecyl 1-methylpiperidine-4-carboxylate.

The lipid complex according to an embodiment contains the above-described cationic lipid in a content of for example, 10 to 100 mol %, 20 to 90 mol %, or 40 to 70 mol % based on the total lipids contained in the lipid complex. One cationic lipid can be used singly, and mixture of two or more cationic lipids can also be used.

The lipid complex according to an embodiment comprises (I) the above-described cationic lipid and (II) at least one lipid selected from the group consisting of neutral lipid, polyethylene glycol-modified lipid, and sterol, as a lipid component. The lipid complex according to an embodiment contains the lipid component in a content of for example, 50 to 99.99% by weight, 70 to 99.9% by weight, or 90 to 99% by weight to the total weight of the lipid complex.

The term "neutral lipid" refers to a lipid present either as a non-charged form or as a neutral zwitterion at physiological pH. Examples of the neutral lipid according to an embodiment include dioleoylphosphatidylethanolamine (DOPE), palmnitoyloleoylphosphatidylcholine (POPC), egg phosphatidylcholine (EPC), dimyristoylphosphatidylcholine (DMPC), dipalmitoylphosphatidylcholine (DPPC), distearoylphosphatidylcholine (DSPC), diarachidoylphosphatidylcholine (DAPC), dibehenoylphosphatidylcholine (DBPC), dilignoceroylphosphatidylcholine (DLPC), dioleoylphosphatidylcholine (DOPC), sphingomyelin, ceramide, dioleoylphosphatidylglycerol (DOPG), dipalmitoylphosphatidylglycerol (DPPG), palmitoyloleoylphosphatidylethanolamine (POPE), and dioleoylphosphatidylethanolamine 4-(N-maleimidomethyl)-cyclohexane-1-carboxylate (DOPE-mal). In an embodiment, the neutral lipid is distearoylphosphatidylcholine (DSPC). One neutral lipid can be used singly, and mixture of two or more neutral lipids can also be used.

The lipid complex according to an embodiment may contain the neutral lipid in a content of for example, 0 to 50 mol %, 0 to 40 mol %, 0 to 30 mol %, or 0 to 20 mol % based on the total lipids contained in the lipid complex.

Examples of the polyethylene glycol-modified lipid (PEG lipid) according to an embodiment include PEG2000-DMG (PEG2000-dimyristyl glycerol), MPEG2000-DMG (MPEG2000-dimyristyl glycerol), PEG2000-DPG (PEG2000-dipalmitoylglycerol), PEG2000-DSG (PEG2000-distearoylglycerol), PEG5000-DMG (PEG5000-dimyristyl glycerol), PEG5000-DPG (PEG5000-dipalmitoylglycerol), PEG5000-DSG (PEG5000-distearoylglycerol), PEG-cDMA (N-[(methoxypoly(ethylene glycol)2000) carbamyl]-1,2-dimyristyloxylpropyl-3-amine), PEG-C-DOMG (R-3-[(co-methoxy-poly(ethylene glycol)2000) carbamoyl)]-1,2-dimyristyloxylpropyl-3-amine), polyethylene glycol (PEG)-diacylglycerol (DAG), PEG-dialkyloxypropyl (DAA), PEG-phospholipid, and PEG-ceramide (Cer). Examples of PEG-dialkyloxypropyl include PEG-dilauryloxypropyl, PEG-dimyristyloxypropyl, PEG-dipalmityloxypropyl, and PEG-disteaiyloxypropyl. In an embodiment, the polyethylene glycol-modified lipid is MPEG2000-DMG (MPEG2000-dimyristyl glycerol). One polyethylene glycol-modified lipid can be used singly, and mixture of two or more polyethylene glycol-modified lipids can also be used.

The lipid complex according to an embodiment may contain the polyethylene glycol-modified lipid in a content of for example, 0 to 30 mol %, 0 to 20 mol %, 0 to 10 mol %, or 0.5 to 2 mol % based on the total lipids contained in the lipid complex.

Sterol is an alcohol having a steroid backbone. Examples of the sterol according to an embodiment include cholesterol, dihydrocholesterol, lanosterol, β-sitosterol, campesterol, stigmasterol, brassicasterol, ergosterol, fucosterol, and 3β-[N—(N',N'-dimethylaminoethyl)carbamoyl]cholesterol (DC-Chol). In an embodiment, the sterol is cholesterol. One sterol can be used singly, and mixture of two or more sterols can also be used.

The lipid complex according to an embodiment may contain the sterol in a content of for example, 0 to 90 mol %, 10 to 80 mol %, or 20 to 40 mol % based on the total lipids contained in the lipid complex.

Combination of lipid components in the lipid complex according to an embodiment is not particularly limited, and examples thereof include combination of the above-described cationic lipid, neutral lipid, and sterol, and combination of the above-described cationic lipid, neutral lipid, polyethylene glycol-modified lipid, and sterol.

The lipid complex according to an embodiment encapsulating the double-stranded ribonucleic acid comprises lipid components of cationic lipid/neutral lipid/polyethylene glycol-modified lipid/sterol, and the mole ratio of the lipids may be, for example, 10 to 99/0 to 50/0 to 10/0 to 50, or 40 to 70/0 to 20/0.5 to 2/20 to 40.

The "average particle size" of the lipid complex particle encapsulating the double-stranded ribonucleic acid according to the present invention refers to the Z-average particle size. The average particle size (Z-average) of a lipid complex according to an embodiment encapsulating the double-stranded ribonucleic acid may be, for example, 10 to 1000 nm, 30 to 500 nm, or 30 to 200 nm as measured by using a particle size analyzer (Malvern Panalytical Ltd., Zetasizer Nano ZS), though the average particle size is not particularly limited thereto.

The siRNA encapsulation efficiency for a lipid complex according to an embodiment encapsulating the double-stranded ribonucleic acid can be calculated, for example, from the siRNA concentration of a formulation diluted with RNase Free Water, which is assumed as the concentration of siRNA present in the LNP external solution, and the siRNA concentration of the formulation diluted with 1% Triton X-100, which is assumed as the total siRNA concentration of the formulation, where each siRNA concentration is measured by using Quant-iT RiboGreen RNA Reagent (Invitrogen, Cat#R11491) (see also Kewal K. Jain, Drug Delivery System, Methods in Molecular Biology, Vol. 1141: 109-120). It is preferable that the encapsulation efficiency calculated in this manner be, for example, higher than 80%, higher than 85%, or higher than 90%. It is preferable that the siRNA encapsulation efficiency for a lipid complex according to an embodiment encapsulating the double-stranded ribonucleic acid be higher than 90%.

<Method for Producing Lipid Complex>

Examples of methods for encapsulating an effective molecule in a lipid complex include a reverse phase evaporation method, a zwitterion (NaCl) hydration method, a cationic core hydration method, and a method with ethanol and calcium (see, Biomembr., 1468, 239-252 (2000)). A lipid complex according to an embodiment encapsulating the double-stranded ribonucleic acid can be prepared by using any of these methods known in the art.

A lipid complex according to an embodiment encapsulating the double-stranded ribonucleic acid can be prepared by, for example, mixing a lipid solution containing the cationic lipid and at least one lipid selected from the group consisting of neutral lipid, polyethylene glycol-modified lipid, and sterol, and an acidic buffer containing the double-stranded ribonucleic acid. By using such a method, a lipid complex the inside of which is filled with a core of the double-stranded ribonucleic acid and the lipids can be obtained. A lipid complex according to an embodiment encapsulating the double-stranded ribonucleic acid may contain the cationic lipid and at least one lipid selected from the group consisting of neutral lipid, polyethylene glycol-modified lipid, and sterol.

A lipid complex according to an embodiment encapsulating the double-stranded ribonucleic acid can be produced by using a method including: a step (a) of mixing a polar organic solvent-containing aqueous solution containing (I) the cationic lipid and (II) at least one lipid selected from the group consisting of neutral lipid, polyethylene glycol-modified lipid, and sterol, and an aqueous solution containing (III) the double-stranded ribonucleic acid to obtain a mixed solution; and a step (b) of reducing the content of the polar organic solvent in the mixed solution.

Through the electrostatic interaction between the double-stranded ribonucleic acid and the cationic lipid, each being water-soluble, and the hydrophobic interaction among the lipids, a lipid complex encapsulating the double-stranded ribonucleic acid in a fine particle comprising the lipids can be formed. For example, a lipid complex can be formed by reducing the content of the polar organic solvent in the mixed solution to change the solubility of the lipid component containing (I) the cationic lipid and (II) at least one lipid selected from the group consisting of neutral lipid, polyethylene glycol-modified lipid, and sterol in the polar organic solvent-containing aqueous solution. Examples of the polar organic solvent include alcohol such as ethanol.

First, in the step (a), a polar organic solvent-containing aqueous solution containing (I) the cationic lipid and (II) at least one lipid selected from the group consisting of neutral lipid, polyethylene glycol-modified lipid, and sterol dissolved therein is mixed with an aqueous solution containing (III) the double-stranded ribonucleic acid to obtain a mixed solution. The concentration of the polar organic solvent in the polar organic solvent-containing aqueous solution is not particularly limited as long as conditions for dissolving lipid molecules are satisfied even after mixing with the aqueous solution containing the double-stranded ribonucleic acid. In an example, the concentration of the polar organic solvent in the polar organic solvent-containing aqueous solution in the step (a) can be 0 to 60% by weight. The aqueous solution containing (III) the double-stranded ribonucleic acid is obtained by, for example, dissolving the double-stranded ribonucleic acid in an acidic buffer.

Subsequently, in the step (b), the content of the polar organic solvent is reduced by adding water or the like to the mixed solution. Thereby, a lipid complex can be formed. It is preferred for efficient formation of the lipid complex to rapidly lower the content of the polar organic solvent. In an example, the concentration of the polar organic solvent in the final polar organic solvent-containing aqueous solution in the step (b) can be 0 to 5% by weight.

The mixed solution obtained in the step (a) may be subjected to dialysis to remove the polar organic solvent and substitute the solvent with a pharmaceutically acceptable medium. The content of the polar organic solvent in the solution decreases during the dialysis, by which a lipid complex can be formed.

By using the method for producing a composition according to an embodiment, a lipid complex encapsulating the double-stranded ribonucleic acid in the inside of a fine particle can be obtained with high encapsulation efficiency.

Examples of the acidic buffer to dissolve the double-stranded ribonucleic acid therein include sulfate buffer, phosphate buffer, phthalate buffer, tartrate buffer, citrate buffer, formate buffer, oxalate buffer, and acetate buffer.

Examples of the solvent to dissolve the lipids therein include polar organic solvent such as alcohol, and the solvent may be, for example, ethanol, isopropanol, chloroform, or tert-butanol.

(Complement C5 Inhibitor and Pharmaceutical Composition)

As described above, expression of complement C5 can be inhibited through RNAi by using the double-stranded ribonucleic acid according to an embodiment. Accordingly, a complement C5 inhibitor and pharmaceutical composition containing a double-stranded ribonucleic acid according to an embodiment or a lipid complex encapsulating the double-stranded ribonucleic acid can be provided. The complement C5 inhibitor and pharmaceutical composition can contain a pharmaceutically acceptable carrier in addition to a double-stranded ribonucleic acid according to an embodiment or a lipid complex encapsulating the double-stranded ribonucleic acid.

Examples of the pharmaceutically acceptable carrier include liquid or solid fillers, diluent, excipients, production aids, and solvent-encapsulating materials.

The pharmaceutical composition according to an embodiment may be, for example, in the form of powder obtained by removing solvent through freeze-drying or the like, or in the form of liquid. A pharmaceutical composition according to an embodiment is a powder composition containing a lipid complex according to any of the above-described embodiments. The powder composition may be prepared by removing solvent from a composition in the form of liquid (dispersion), for example, through filtration or centrifugation, or prepared by freeze-drying the dispersion. In the case that the pharmaceutical composition is in the form of powder, the pharmaceutical composition can be suspended or dissolved in a pharmaceutically acceptable medium before use and used as an injection. A pharmaceutical composition according to an embodiment is a liquid composition containing a lipid complex according to any of the above-described embodiments and a pharmaceutically acceptable medium. In the case that the pharmaceutical composition is in the form of liquid, the pharmaceutical composition can be directly used as an injection, or suspended or dissolved in a pharmaceutically acceptable medium and used as an injection.

By administering a complement C5 inhibitor or pharmaceutical composition according to an embodiment to a subject in need thereof expression of complement C5 in the subject can be inhibited through RNAi. Here, the "subject in need thereof" refers to a subject presenting with a disease or disorder associated with expression or activity of the C5 gene, or a subject determined to have a high risk of development thereof In some embodiments, the double-stranded ribonucleic acid can inhibit expression of complement C5, and hence a complement C5 inhibitor or pharmaceutical composition containing the double-stranded ribonucleic acid or a lipid complex encapsulating the double-stranded ribonucleic acid can be useful for treating paroxysmal nocturnal hemoglobinuria (PNH) and atypical hemolytic uremic syndrome (aHUS). Thus, in other embodiments, a method for treating paroxysmal nocturnal hemoglobinuria or atypical hemolytic uremic syndrome, the method including a step of administering a therapeutically effective amount of a complement C5 inhibitor or pharmaceutical composition according to an embodiment, is provided. In other embodiments, use of the double-stranded ribonucleic acid according to an embodiment or a lipid complex encapsulating the double-stranded ribonucleic acid according to an embodiment for producing a therapeutic drug for paroxysmal nocturnal hemoglobinuria or atypical hemolytic uremic syndrome, is provided. In other embodiments, the double-stranded ribonucleic acid according to an embodiment or a lipid complex encapsulating the double-stranded ribonucleic acid according to an embodiment for use in a method for treating paroxysmal nocturnal hemoglobinuria or atypical hemolytic uremic syndrome, is provided.

The double-stranded ribonucleic acid according to an embodiment or a lipid complex encapsulating the double-stranded ribonucleic acid according to an embodiment in the lipid complex can be used singly or in combination with another agent or composition in a therapeutic method. For example, the double-stranded ribonucleic acid according to an embodiment or a lipid complex encapsulating the double-stranded ribonucleic acid according to an embodiment may be administered simultaneously with or separately from administration of another agent. Such combination therapy includes combined administration (two or more agents are contained in one formulation or different formulations) and separate administration (e.g., simultaneous or sequential). If two or more agents are to be separately administered, the double-stranded ribonucleic acid according to an embodiment or a lipid complex encapsulating the double-stranded ribonucleic acid according to an embodiment may be administered prior to or sequentially after the accompanying therapeutic method.

The subject to administer a complement C5 inhibitor or pharmaceutical composition containing the double-stranded ribonucleic acid according to an embodiment or a lipid complex encapsulating the double-stranded ribonucleic acid according to an embodiment is not limited, and, for example, the subject can be humans or non-human mammals (such as monkeys, mice, rats, rabbits, cows, horses, goats).

The method for administering a complement C5 inhibitor or pharmaceutical composition containing the double-stranded ribonucleic acid according to an embodiment or a lipid complex encapsulating the double-stranded ribonucleic acid according to an embodiment to a subject (such as the route of administration, dose, frequency of administration per day, timing of administration) is not limited, and can be appropriately determined by one of ordinary skill in the art (e.g., physicians) in accordance with the health condition of a subject, the degree of a disease, the type of an agent to be used in combination.

(Administration Method)

The mode of administration of a complement C5 inhibitor and pharmaceutical composition according to an embodiment is not particularly limited, and may be parenteral administration, and examples thereof include intravenous administration, intramuscular administration, subcutaneous administration, intradermal administration, and intrathecal administration.

A complement C5 inhibitor and pharmaceutical composition according to an embodiment can be administered in an amount enough to inhibit complement C5 depending on the mode of administration. The dose of a complement C5 inhibitor and pharmaceutical composition according to an embodiment may be, for example, 0.01 mg to 100 mg, or 0.1 mg to 50 mg, or 0.3 mg to 10 mg, per kg body weight of a subject.

One of ordinary skill in the art understand that the present invention may be implemented with appropriate combination of any one or more of all the embodiments described herein, unless the combination causes any technical contradiction. In addition, one of ordinary skill in the art understand that it would be preferred to implement the present invention with appropriate combination of any of all the preferred or advantageous embodiments described herein, unless the combination causes any technical contradiction.

All of the contents disclosed in the literatures mentioned herein are incorporated by reference in their entirety, and one of ordinary skill in the art can cite and understand related contents disclosed in the literatures as a part of the present specification in accordance with the context of the present specification, without departing from the spirit and scope of the present invention.

The literatures cited herein are provided only for the purpose of disclosing related art before the filing date of the present application, and should not be interpreted as admission that the present inventors have no right of priority to the disclosures because of any prior invention or for any other reason. All of the descriptions in the literatures are based on information which was available for the applicant, and by no means constitute admission that the described contents are correct.

The terms used herein are for describing specific embodiments, and not intended to limit the invention.

The term "comprise" used herein is intended to indicate the presence of a mentioned matter (e.g., a member, a step, an element, or a number) unless the context apparently requires different understanding, and does not exclude the presence of another matter (e.g., a member, a step, an element, or a number). The term "consist of" encompasses embodiments described with the term(s) "consist of" and/or "consist essentially of".

Unless otherwise defined, all terms used herein (including technical terms and scientific terms) have the same meaning as commonly understood by one of ordinary skill in the art to which the present invention pertains. Each of the terms used herein should be interpreted to have a meaning consistent with that in the present specification and in the fields of related art unless otherwise specified, and should not be interpreted with respect to an idealized or excessively literal meaning.

While terms such as "first" and "second" are used to represent various elements, it is to be understood that such elements should not be limited by the terms themselves. The terms are used only to distinguish one element from another element, and, for example, it is acceptable without departing from the scope of the present invention to express a first element as "second element" and to express a second element as "first element", similarly.

Numerical values used herein to indicate component contents, numerical ranges, and so forth should be understood to be modified with the term "approximately", unless otherwise specified. For example, "4° C." is understood to refer to "approximately 4° C.", unless otherwise specified, and, needless to say, one of ordinary skill in the art can rationally understand the allowance in accordance with the common general knowledge and the context of the present specification.

Unless the context clearly indicates otherwise, embodiments with a singular form as used herein and in the claims are to be understood to allow the plural form, and vice versa, as long as no technical contradiction is caused.

Hereinafter, the present invention will be described in more detail with reference to Examples. However, the present invention can be realized in various embodiments, and should not be interpreted to be limited to Examples described below. One of ordinary skill in the art can implement the present invention with various modifications, additions, deletions, substitutions, and so forth, without changing the spirit or scope of the present invention.

EXAMPLES

Example 1: In-Vitro Screening for Single Administration (1)

(Preparation of Double-Stranded Nucleic Acids)

Sense strands and antisense strands listed in Table 2 were synthesized by using the phosphoramidite method, and then annealed to synthesize double-stranded nucleic acids (GeneDesign, Inc.). Abbreviations in the sequences are as shown in Table 1. Each double-stranded nucleic acid synthesized had a hydroxy group instead of a phosphate group at each 3'-terminal.

TABLE 1

| Abbreviation | Nucleotide |
| --- | --- |
| A | Adenosine-3'-phosphate |
| U | Uridine-3'-phosphate |
| G | Guanosine-3'-phosphate |
| C | Cytidine-3'-phosphate |
| a | 2'-O-methyladenosine-3'-phosphate |
| u | 2'-O-methyluridine-3'-phosphate |
| g | 2'-O-methylguanosine-3'-phosphate |
| c | 2'-O-methylcytidine-3'-phosphate |
| dT | Deoxy-thymidine |
| (idT) | Inverted deoxy-thymidine (inverted dT) |
| ^ | Phosphorothioate bond |

No symbol indicates that nucleotides are linked together via a phosphodiester bond

TABLE 2

| Double strand ID | Numbers of nucleotides in sense strand/antisense strand | Sense strand Sequence (5'→3') | SEQ ID NO | Antisense strand Sequence (5'→3') | SEQ ID NO | Target site in NM_001735.2 |
|---|---|---|---|---|---|---|
| siRNA-001 | 21/21 | AGGcAAAGGuGuucAAAGAdT^dT | 1 | UCUUUGAAcACCUUUGCCUdT^dT | 2 | 2477-2495 |
| siRNA-002 | 21/21 | cuGucuuAAcuuucAuAGAdT^dT | 3 | UCuAUGAAAGUuAAGAcAGdT^dT | 4 | 506-524 |
| siRNA-003 | 21/21 | uAGcAuGuGccAGcuAcAAdT^dT | 5 | UUGuAGCUGGcAcAUGCuAdT^dT | 6 | 4238-4256 |
| siRNA-004 | 21/21 | cuGuGAuuGGAAuuAGAAAdT^dT | 7 | UUUCuAAUUCcAAUcAcAGdT^dT | 8 | 3473-3491 |
| siRNA-006 | 21/21 | AAGGcAAAGGuGuucAAAGdT^dT | 9 | CUUUGAAcACCUUUGCCUUdT^dT | 10 | 2476-2494 |
| siRNA-007 | 21/21 | GAAAGGAAcuGuuuAcAAcdT^dT | 11 | GUUGuAAAcAGUUCCUUUCdT^dT | 12 | 2553-2571 |
| siRNA-008 | 21/21 | uGGuAuAuGuGuuGcuGAudT^dT | 13 | AUcAGcAAcAcAuAuACCAdT^dT | 14 | 2451-2469 |
| siRNA-009 | 21/21 | AcuGucuuAAcuuucAuAGdT^dT | 15 | CuAUGAAAGUuAAGAcAGUdT^dT | 16 | 505-523 |
| siRNA-010 | 21/21 | GuGccAGcuAcAAGcccAGdT^dT | 17 | CUGGGCUUGuAGCUGGcACdT^dT | 18 | 4244-4262 |
| siRNA-011 | 21/21 | AAGGAAcuGuuuAcAAcuAdT^dT | 19 | uAGUUGuAAAcAGUUCCUUdT^dT | 20 | 2555-2573 |
| siRNA-012 | 21/21 | uccucuGGAAauuGGccuudT^dT | 21 | AAGGCcAAUUUCcAGAGGAdT^dT | 22 | 2733-2751 |
| siRNA-013 | 21/21 | uuGAAAGGAAcuGuuuAcAdT^dT | 23 | UGuAAAcAGUUCCUUUcAAdT^dT | 24 | 2551-2569 |
| siRNA-014 | 21/21 | AAAGGAAcuGuuuAcAAcudT^dT | 25 | AGUUGuAAAcAGUUCCUUUdT^dT | 26 | 2554-2572 |
| siRNA-015 | 21/21 | AGGAAcuGuuuAcAAcuAudT^dT | 27 | AuAGUUGuAAAcAGUUCCUdT^dT | 28 | 2556-2574 |
| siRNA-016 | 21/21 | uAcAcuGAAGcAuuuGAuGdT^dT | 29 | cAUcAAAUGCUUcAGUGuAdT^dT | 30 | 166-184 |
| siRNA-017 | 21/21 | cAcuGAAGcAuuuGAuGcAdT^dT | 31 | UGcAUcAAAUGCUUcAGUGdT^dT | 32 | 168-186 |
| siRNA-018 | 21/21 | cuGAAGcAuuuGAuGcAAcdT^dT | 33 | GUUGcAUcAAAUGCUUcAGdT^dT | 34 | 170-188 |
| siRNA-019 | 21/21 | uucuGcAAcuGAAuucGAudT^dT | 35 | AUCGAAUUcAGUUGcAGAAdT^dT | 36 | 4412-4430 |
| siRNA-020 | 21/21 | uGAAAGGAAcuGuuuAcAAdT^dT | 37 | UUGuAAAcAGUUCCUUUcAdT^dT | 38 | 2552-2570 |
| siRNA-021 | 21/21 | AcuGAAGcAuuuGAuGcAAdT^dT | 39 | UUGcAUcAAAUGCUUcAGUdT^dT | 40 | 169-187 |
| siRNA-022 | 21/21 | cAuAcAGAcAAAccuGuuudT^dT | 41 | AAAcAGGUUUGUCUGuAUGdT^dT | 42 | 415-433 |
| siRNA-023 | 21/21 | AAAcAAcAAGuAccuuuAudT^dT | 43 | AuAAAGGuACUUGUUGUUUdT^dT | 44 | 984-1002 |
| siRNA-024 | 21/21 | AuAcAGAcAAAccuGuuuAdT^dT | 45 | uAAAcAGGUUUGUCUGuAUdT^dT | 46 | 416-434 |
| siRNA-025 | 21/21 | GGuAuAuGuGuuGcuGAudT^dT | 47 | uAUcAGcAAcAcAuAuACCdT^dT | 48 | 2452-2470 |
| siRNA-026 | 21/21 | ucAGAAAGucuGuGAAGGAdT^dT | 49 | UCCUUcAcAGACUUUCUGAdT^dT | 50 | 4578-4596 |
| siRNA-027 | 21/21 | ucuccAGGccAAAcuGuGudT^dT | 51 | AcAcAGUUUGGCCUGGAGAdT^dT | 52 | 1777-1795 |
| siRNA-028 | 21/21 | AcAAcAAGuAccuuuAuAudT^dT | 53 | AuAuAAAGGuACUUGUUGUdT^dT | 54 | 986-1004 |
| siRNA-029 | 21/21 | cAAcAAGuAccuuuAuAuudT^dT | 55 | AAuAuAAAGGuACUUGUUGdT^dT | 56 | 987-1005 |
| siRNA-030 | 21/21 | AuuccccAGGccAAAcuGudT^dT | 57 | AcAGUUUGGCCUGGAGAAUdT^dT | 58 | 1775-1793 |
| siRNA-031 | 21/21 | GuGGcAccAGcuccAGGudT^dT | 59 | ACCUGGAGCUGGUUGCcACdT^dT | 60 | 1730-1748 |
| siRNA-032 | 21/21 | AAGAGAcAucuGAcuuGGAdT^dT | 61 | UCcAAGUcAGAUGUCUCUUdT^dT | 62 | 1226-1244 |
| siRNA-033 | 21/21 | AuucuGcAAcuGAAuucGAdT^dT | 63 | UCGAAUUcAGUUGcAGAAUdT^dT | 64 | 4411-4429 |
| siRNA-034 | 21/21 | uuccucuGGAAAuuGGccudT^dT | 65 | AGGCcAAUUUCcAGAGGAAdT^dT | 66 | 2732-2750 |
| siRNA-035 | 21/21 | AAcAAcAAGuAccuuuAuAdT^dT | 67 | uAuAAAGGuACUUGUUGUUdT^dT | 68 | 985-1003 |

TABLE 2-continued

| Double strand ID | Numbers of nucleotides in sense strand/antisense strand | Sense strand Sequence (5'→3') | SEQ ID NO | Antisense strand Sequence (5'→3') | SEQ ID NO | Target site in NM_001735.2 |
|---|---|---|---|---|---|---|
| siRNA-036 | 21/21 | AAuAuGuccucucucccuAdT^dT | 69 | uAGGGAGAGAGGAcAuAUUdT^dT | 70 | 1067-1085 |
| siRNA-037 | 21/21 | AcucAcuAuAAuuAcuuGAdT^dT | 71 | UcAAGuAAUuAuAGUGAGUdT^dT | 72 | 1519-1537 |
| siRNA-038 | 21/21 | AuAAcucAcuAuAAuuAcudT^dT | 73 | AGuAAUuAuAGUGAGUuAUdT^dT | 74 | 1516-1534 |
| siRNA-039 | 21/21 | AAAuAuGuccucucucccudT^dT | 75 | AGGGAGAGAGGAcAuAUUUdT^dT | 76 | 1066-1084 |
| siRNA-040 | 21/21 | AAGAuAuuuuuAuAAuAAAdT^dT | 77 | UUuAUuAuAAAAAuAUCUUdT^dT | 78 | 876-894 |
| siRNA-042 | 21/21 | AAAAuAAcucAcuAuAAuudT^dT | 79 | AAUuAuAGUGAGUuAUUUUdT^dT | 80 | 1513-1531 |
| siRNA-043 | 21/21 | AAAuAAcucAcuAuAAuuAdT^dT | 81 | uAAUuAuAGUGAGUuAUUUdT^dT | 82 | 1514-1532 |
| siRNA-044 | 21/21 | GuGuuAAAAuGucuGcuGudT^dT | 83 | AcAGcAGAcAUUUuAAcACdT^dT | 84 | 2597-2615 |
| siRNA-045 | 21/21 | AAAAuGuuuuuGucAAGuAdT^dT | 85 | uACUUGAcAAAAAcAUUUUdT^dT | 86 | 4742-4760 |
| Mock | 21/21 | cuuAcGcuGAGuAcuucGAdT^dT | 87 | UCGAAGuACUcAGCGuAAGdT^dT | 88 | — |

(In-Vitro Screening)

Each of the double-stranded nucleic acids listed in Table 2 in combination with the transfection reagent Lipofectamine RNAiMax (from Invitrogen, catalog number: 13778150) was diluted with an Opti-MEM medium (from Gibco, catalog number: 31985062) to prepare siRNA/RNAiMax mixed solution with a final concentration of 3 nM double-stranded nucleic acid and 0.3% RNAiMax. The siRNA/RNAiMax mixed solution was aliquoted into 20 μL portions in wells of a 96-well culture plate, and Hep3B cells (obtained from ATCC) as cell lines derived from human liver cancer were seeded in each well at 20000 cells/80 μL/well, and cultured under conditions of 37° C. and 5% $CO_2$ overnight. From the cultured cells, a template lysate for real-time PCR was prepared by using a CellAmp (registered trademark) Direct RNA Prep Kit for RT-PCR (Real Time) (from Takara Bio Inc., catalog number: 3732) and Proteinase K (from Takara Bio Inc., catalog number: 9034) in accordance with a protocol provided by Takara Bio Inc. Thereafter, cDNA was prepared by using a PrimeScript (registered trademark) RT Master Mix (Perfect Real Time) (from Takara Bio Inc., catalog number: RR036A) in accordance with a protocol provided by Takara Bio Inc. Further, Ct values were measured for the target gene human C5 and the endogenous control gene human GAPDH (glyceraldehyde-3-phosphate dehydrogenase) by using an EagleTaq Universal Master Mix (ROX) (from Roche Diagnostics K.K., catalog number: 07260296190) and a TaqMan probe (from Applied Biosystems, C5: Hs00156197_m1; GAPDH: Hs02758991_g1) with an ABI7900HT real-time PCR system (from Applied Biosystems) in accordance with a protocol provided by Applied Biosystems. The C5 mRNA expression level in the case that Hep3B cells were treated only with the transfection reagent without addition of siRNA was defined as 100%, and a C5 mRNA residual rate (relative value) was calculated for each introduction of siRNA by using a calibration curve method. As a negative control, Mock which does not cross over with any human gene was used.

The results are shown in Table 3.

TABLE 3

| Double strand ID | C5 mRNA residual rate (n = 3, average) (3nM siRNA) |
|---|---|
| siRNA-001 | 18% |
| siRNA-002 | 43% |
| siRNA-003 | 107% |
| siRNA-004 | 35% |
| siRNA-006 | 37% |
| siRNA-007 | 28% |
| siRNA-008 | 18% |
| siRNA-009 | 89% |
| siRNA-010 | 107% |
| siRNA-011 | 107% |
| siRNA-012 | 37% |
| siRNA-013 | 53% |
| siRNA-014 | 64% |
| siRNA-015 | 125% |
| siRNA-016 | 35% |
| siRNA-017 | 26% |
| siRNA-018 | 48% |
| siRNA-019 | 27% |
| siRNA-020 | 42% |
| siRNA-021 | 74% |
| siRNA-022 | 39% |
| siRNA-023 | 101% |
| siRNA-024 | 41% |
| siRNA-025 | 125% |
| siRNA-026 | 41% |
| siRNA-027 | 143% |
| siRNA-028 | 61% |
| siRNA-029 | 40% |
| siRNA-030 | 151% |
| siRNA-031 | 96% |
| siRNA-032 | 73% |
| siRNA-033 | 70% |
| siRNA-034 | 121% |
| siRNA-035 | 54% |
| siRNA-036 | 119% |

TABLE 3-continued

| Double strand ID | C5 mRNA residual rate (n = 3, average) (3nM siRNA) |
|---|---|
| siRNA-037 | 119% |
| siRNA-038 | 47% |
| siRNA-039 | 100% |
| siRNA-040 | 111% |
| siRNA-042 | 112% |
| siRNA-043 | 53% |
| siRNA-044 | 87% |
| siRNA-045 | 115% |
| Mock | 116% |
| Lipofection only | 100% |

Example 2: In-Vitro Screening for Single Administration (2)

(Preparation of Double-Stranded Nucleic Acids)

Sense strands and antisense strands listed in Table 4 were synthesized by using the phosphoramidite method, and then annealed to synthesize double-stranded nucleic acids (GeneDesign, Inc.).

TABLE 4

| Double strand ID | Numbers of nucleotides in sense strand/antisense strand | Sense strand Sequence (5'→3') | SEQ ID NO | Antisense strand Sequence (5'→3') | SEQ ID NO |
|---|---|---|---|---|---|
| siRNA-001 | 21/21 | AGGcAAAGGuGuucAAAGAdT^dT | 89 | UCUUUGAAcACCUUUGCCUdT^dT | 90 |
| siRNA-001-02 | 19/19 | AGGcAAAGGuGuucAAAGA | 91 | UCUUUGAAcACCUUUGCCU | 92 |
| siRNA-001-08 | 21/21 | A^GGcAAAGGuGuucAAAGAuu | 93 | U^CUUUGAAcACCUUUGCCUuu | 94 |
| siRNA-001-09 | 21/21 | A^G^GcAAAGGuGuucAAAGAuu | 95 | U^C^UUUGAAcACCUUUGCCUuu | 96 |
| siRNA-001-10 | 21/21 | A^GGcAAAGGuGuucAAAGA^u^u | 98 | U^CUUUGAAcACCUUUGCCU^u^u | 98 |
| siRNA-001-11 | 19/21 | AGGcAAAGGuGuucAAAGA | 99 | UCUUUGAAcACCUUUGCCUuu | 100 |
| siRNA-001-12 | 21/21 | AuAGGcAAAGGuGuucAAAGA | 101 | UCUUUGAAcACCUUUGCCUuu | 102 |
| siRNA-001-13 | 22/21 | uAuAGGcAAAGGuGuucAAAGA | 103 | UCUUUGAAcACCUUUGCCUuu | 104 |
| siRNA-006 | 21/21 | AAGGcAAAGGuGuucAAAGdT^dT | 105 | CUUUGAAcACCUUUGCCUUdT^dT | 106 |
| siRNA-006-02 | 19/19 | AAGGcAAAGGuGuucAAAG | 107 | CUUUGAAcACCUUUGCCUU | 108 |
| siRNA-007 | 21/21 | GAAAGGAcuGuuuAcAAcdT^dT | 109 | GUUGuAAAcAGUUCCUUUCdT^dT | 110 |
| siRNA-007-02 | 19/19 | GAAAGGAcuGuuuAcAAc | 111 | GUUGuAAAcAGUUCCUUUC | 112 |
| siRNA-008 | 21/21 | uGGuAuAuGuGuuGcuGAudT^dT | 113 | AUcAGcAAcAcAuAuACcAdT^dT | 114 |
| siRNA-008-02 | 19/19 | uGGuAuAuGuGuuGcuGAu | 115 | AUcAGcAAcAcAuAuACcA | 116 |
| siRNA-008-08 | 21/21 | u^GGuAuAuGuGuuGcuGAuuu | 117 | A^UcAGcAAcAcAuAuACcAuu | 118 |
| siRNA-008-09 | 21/21 | u^G^GuAuAuGuGuuGcuGAuuu | 119 | A^U^cAGcAAcAcAuAuACcAuu | 120 |
| siRNA-008-10 | 21/21 | u^GGuAuAuGuGuuGcuGAu^u^u | 121 | A^UcAGcAAcAcAuAuACcA^u^u | 122 |
| siRNA-008-11 | 19/21 | uGGuAuAuGuGuuGcuGAu | 123 | AUcAGcAAcAcAuAuACcAuu | 124 |
| siRNA-008-12 | 21/21 | AuuGGuAuAuGuGuuGcuGAu | 125 | AUcAGcAAcAcAuAuACcAuu | 126 |
| siRNA-008-13 | 22/21 | uAuuGGuAuAuGuGuuGcuGAu | 127 | AUcAGcAAcAcAuAuACcAuu | 128 |
| siRNA-008-14 | 23/21 | uAuuGGuAuAuGuGuuGcuGAu(idT) | 129 | AUcAGcAAcAcAuAuACcAuu | 130 |
| siRNA-008-22 | 21/21 | uGGuAuAuGuGuuGCuGAuuu | 131 | AUcAGcAAcAcAuAuACcAuu | 132 |
| siRNA-008-23 | 21/21 | uGGuAuAuGuGuuGcUGAuuu | 133 | AUcAGcAAcAcAuAuACcAuu | 134 |
| siRNA-008-29 | 20/20 | AuuGGuAuAuGuGuuGcuGA | 135 | UcAGcAAcAcAuAuACcAuu | 136 |
| siRNA-008-30 | 20/20 | AuGGuAuAuGuGuuGcuGAu | 137 | AUcAGcAAcAcAuAuACcuu | 138 |

TABLE 4-continued

| Double strand ID | Numbers of nucleotides in sense strand/antisense strand | Sense strand Sequence (5'→3') | SEQ ID NO | Antisense strand Sequence (5'→3') | SEQ ID NO |
|---|---|---|---|---|---|
| siRNA-008-31 | 19/23 | uGGuAuAuGuGuuGcuGAu | 139 | AUcAGcAAcAcAuAuACcAuuuu | 140 |
| siRNA-008-32 | 19/23 | uGGuAuAuGuGuuGCuGAu | 141 | AUcAGcAAcAcAuAuACcAuuuu | 142 |
| siRNA-008-33 | 19/23 | uGGuAuAuGuGuuGCuGAu | 143 | AUcAGcAAcAcAuAuACcAuuaa | 144 |
| siRNA-008-34 | 19/23 | uGGuAuAuGuGuuGCuGAu | 145 | AUcAGcAAcAcAuAuACcAuu^a^a | 146 |
| siRNA-008-35 | 19/23 | uGGuAuAuGuGuuGCuGAu | 147 | AUcAGcAAcAcAuAuACcA^u^uaa | 148 |
| siRNA-008-36 | 19/23 | uGGuAuAuGuGuuGCuGAu | 149 | a^UcAGcAAcAcAuAuACcA^u^uaa | 150 |
| siRNA-008-37 | 19/23 | uGGuAuAuGuGuuGCuGAu | 151 | aUcAGcAAcAcAuAuACcAuuuu | 152 |
| siRNA-008-38 | 19/23 | u^GGuAuAuGuGuuGCuGAu | 153 | AUcAGcAAcAcAuAuACcA^u^uaa | 154 |
| siRNA-038 | 21/21 | AuAAcucAcuAuAAuuAcudT^dT | 155 | AGuAAUuAuAGUGAGUuAUdT^dT | 156 |
| siRNA-038-02 | 19/19 | AuAAcucAcuAuAAuuAcu | 157 | AGuAAUuAuAGUGAGUuAU | 158 |
| Mock | 21/21 | cuuAcGcuGAGuAcuucGAdT^dT | 87 | UCGAAGuACUcAGCGuAAGdT^dT | 88 |

(In-Vitro Screening)

A test was performed to measure Ct values for the target gene human C5 and the endogenous control gene human GAPDH in cultured Hep3B cells in the same manner as in Example 1, except that siRNA/RNAiMax mixed solution was prepared with a final concentration of 1 nM double-stranded nucleic acid and 0.3% RNAiMax. As in Example 1, the C5 mRNA expression level in the case of Lipofection only was defined as 100%, and a C5 mRNA residual rate (relative value) was calculated for each introduction of siRNA.

The results are shown in Table 5. Lowered C5 mRNA residual rates were found for all of the double-stranded nucleic acids except siRNA-008-29, demonstrating that expression of C5 was suppressed.

TABLE 5

| Double strand ID | C5 mRNA residual rate (n = 3, average) (1nM siRNA) |
|---|---|
| siRNA-001 | 36% |
| siRNA-001-02 | 44% |
| siRNA-001-08 | 42% |
| siRNA-001-09 | 42% |
| siRNA-001-10 | 44% |
| siRNA-001-11 | 45% |
| siRNA-001-12 | 39% |
| siRNA-001-13 | 45% |
| siRNA-006 | 43% |
| siRNA-006-02 | 40% |
| siRNA-007 | 44% |
| siRNA-007-02 | 50% |
| siRNA-008 | 34% |
| siRNA-008-02 | 37% |
| siRNA-008-08 | 37% |
| siRNA-008-09 | 41% |
| siRNA-008-10 | 45% |
| siRNA-008-11 | 38% |
| siRNA-008-12 | 39% |
| siRNA-008-13 | 46% |
| siRNA-008-14 | 42% |
| siRNA-008-22 | 37% |
| siRNA-008-23 | 36% |
| siRNA-008-29 | 119% |
| siRNA-008-30 | 33% |
| siRNA-008-31 | 36% |
| siRNA-008-32 | 39% |
| siRNA-008-33 | 36% |
| siRNA-008-34 | 32% |
| siRNA-008-35 | 33% |
| siRNA-008-36 | 37% |
| siRNA-008-37 | 34% |
| siRNA-008-38 | 38% |
| siRNA-038 | 43% |
| siRNA-038-02 | 54% |
| Mock | 90% |
| Lipofection only | 100% |

Example 3: In-Vivo Screening (Sequence Finding)

(Preparation of siRNA-LNPs)

Each siRNA listed in Table 6 was dissolved in 10 mM sodium citrate (pH 4.0) to prepare diluted siRNA solution. Lipid solution was prepared by dissolving 2-{9-oxo-9-[(3-pentyloctyl)oxy]nonyl}dodecyl 1-methylpiperidine-4-carboxylate, DSPC (NIPPON FINE CHEMICAL CO., LTD.), Cholesterol (NIPPON FINE CHEMICAL CO., LTD.), and MPEG2000-DMG (NOF CORPORATION) at a mole ratio of 60/10.5/28/1.5 in ethanol. Lipid Nanoparticles (LNPs) were obtained by mixing the diluted siRNA solution and the lipid solution at flow rates of 3 mL/min and 1 mL/min, respectively, with an siRNA/lipid weight ratio of 0.1. The external solution of the resulting LNP aqueous solution was substituted with PBS (pH 7.4) through dialysis by using a Float-A-Lyzer G2 (SPECTRUM, 100K MWCO). After the dialysis, the resultant was subjected to concentration and filtration sterilization for use in experiments. The siRNA concentration and encapsulation efficiency were measured by using a Quant-iT RiboGreen RNA Reagent (Invitrogen, Cat#R11491). For calculation of the encapsulation efficiency, the siRNA concentration measured after dilution with RNase Free Water was assumed as the concentration of siRNA present in the LNP external solution, and the siRNA concentration measured after dilution with 1% Triton X-100 was assumed as the total siRNA concentration of the formulation. The average particle size (Z-average) was measured by using a particle size analyzer (Malvern Panalytical Ltd., Zetasizer Nano ZS). Results of evaluation of product quality for the prepared LNPs are shown in Table 7.

TABLE 8

| Double strand ID | Liver C5 mRNA residual rate 5 days after administiation (n = 3, Average) | Liver C5 mRNA residual rate 14 days after administration (n = 3, Average) |
| --- | --- | --- |
| PBS | 100% | Not tested |
| Mock | 75% | 105% |
| siRNA-001-01 | 51% | 104% |
| siRNA-007-01 | 69% | 92% |
| siRNA-008-01 | 21% | 62% |

The blood sampled on each sampling day was centrifuged at 3000 rpm for 15 minutes, and then the heparin plasma as

TABLE 6

| Double strand ID | Numbers of nucleotides in sense strand/antisense strand | Sense strand Sequence (5'→3') | SEQ ID NO | Antisense strand Sequence (5'→3') | SEQ ID NO |
| --- | --- | --- | --- | --- | --- |
| Mock | 21/21 | cuuAcGcuGAGuAcuucGAdT^dT | 87 | UCGAAGuACUcAGCGuAAGdT^dT | 88 |
| siRNA-001-01 | 21/21 | AGGcAAAGGuGuucAAAGAuu | 161 | UCUUUGAAcACCUUUGCCUuu | 162 |
| siRNA-007-01 | 21/21 | GAAAGGAAcuGuuuAcAAcuu | 163 | GUUGuAAAcAGUUCCUUUCuu | 164 |
| siRNA-008-01 | 21/21 | uGGuAuAuGuGuuGcuGAuuu | 159 | AUcAGcAAcAcAuAuACcAuu | 160 |

TABLE 7

| Double strand ID | Encapsulation efficiency | Average particle size (nm) | Polydispersity index |
| --- | --- | --- | --- |
| Mock | >90% | 92 | 0.06 |
| siRNA-001-01 | >90% | 90 | 0.08 |
| siRNA-007-01 | >90% | 87 | 0.06 |
| siRNA-008-01 | >90% | 88 | 0.1 |

(In-Vivo Screening)

LNPs encapsulating PBS or siRNA listed in Table 6 therein were intravenously administered to a BALB/c mouse (male, 6 weeks old, n=3 per group) from the tail vein at a dose of 0.1 mg/kg siRNA, and the blood and liver were sampled under anesthesia 5 days and 14 days after the administration. From the liver frozen with liquid nitrogen, Total RNA was purified by using an RNeasy Plus Mini Kit (Qiagen, Cat#74106) in accordance with a protocol provided by the manufacturer. Thereafter, cDNA was prepared by using a PrimeScript RT Master Mix (Perfect Real Time) (Takara Bio Inc., Cat#RR036A) in accordance with a protocol provided by the manufacturer. Further, Ct values were measured for the target gene mouse C5 and the endogenous control gene mouse GAPDH by using a TaqMan (registered trademark) Gene Expression Master Mix (Applied Biosystem, Cat#4369510) and a TaqMan probe (Applied Biosystems, C5: Mm01336776_g1; GAPDH: Mm99999915_g1) with an ABI7500 Fast (Applied Biosystems) in accordance with a protocol provided by the manufacturer. The liver C5 mRNA residual rate 5 days after the administration for the PBS administration group was defined as 100%, and a liver C5 mRNA residual rate (relative value) was calculated for each siRNA administration group by using the comparative Ct method. The results are shown in Table 8.

the supernatant was collected and stored at −80° C. Thereafter, the plasma Mouse C5 was quantified by ELISA. Specifically, the mouse anti-C5 antibody BB5.1 (Hycult Biotech, Cat#HM1073-FS) as an immobilized antibody was diluted with PBS(−) (Wako Pure Chemical Industries, Ltd., #045-29795) to a final concentration of 2 μg/mL and added to an assay plate (Nunc, Cat#442404), and incubated at 4° C. overnight. Thereafter, blocking solution (PBS(−) (Wako Pure Chemical Industries, Ltd.) containing 1% BSA (R&D systems, Inc., Cat#DY995)) was added, and the resultant was incubated at room temperature for 1 hour. The blocking solution was discarded, and washing was performed three times with washing solution (PBS(−) (Wako Pure Chemical Industries, Ltd.) containing 0.02% Tween20). The washing solution was discarded, and the heparin plasma sample diluted with blocking solution was then added, and the resultant was incubated at room temperature for 5 hours. The plasma of the PBS administration group was used as a standard sample. The sample was discarded, and washing was then performed five times with washing solution, and a goat anti-human C5 antibody (Quidel Corporation, Cat#A306) diluted 4000-fold with blocking solution was added, and the resultant was incubated at room temperature for 1 hour. The antibody was discarded, and washing was then performed five times with washing solution, and an HRP-labeled donkey anti-goat IgG (H+L) (Jackson ImmunoResearch Inc., Cat#805-035-180) diluted 40000-fold with blocking solution was added, and the resultant was incubated at room temperature for 1 hour. The antibody was discarded, and washing was then performed five times with washing solution. Thereafter, equal amounts of TMB (3,3', 5,5'-tetramethylbenzidine) Peroxidase Substrate (Kirkegaard & Perry Laboratories, Inc., Cat#50-76-01) and Peroxidase Substrate Solution B (Kirkegaard & Perry Laboratories, Inc., Cat#50-65-00) were mixed together as detection reagent, which was added and allowed to develop color. $H_2SO_4$ (Wako Pure Chemical Industries, Ltd., Cat#198-09595) was added as quenching solution, and absorbance was then measured at 450 nm and 650 nm. Relative values for the samples as the plasma C5 concentration 5 days after the administration for the PBS administration group was defined as 100% are shown in Table 9.

TABLE 9

| Double strand ID | Blood C5 protein residual rate 5 days after administration (n = 3, Average) | Blood C5 protein residual rate 14 days after administration (n = 3, Average) |
| --- | --- | --- |
| PBS | 100% | Not tested |
| Mock | 94% | 96% |
| siRNA-001-01 | 44% | 87% |
| siRNA-007-01 | 79% | 103% |
| siRNA-008-01 | 22% | 48% |

Example 4: In-Vitro Screening

Sense strands and antisense strands listed in Table 10 were synthesized by using the phosphoramidite method, and then annealed to synthesize double-stranded nucleic acids (GeneDesign, Inc.). A test was performed to measure Ct values for the target gene human C5 and the endogenous control gene human GAPDH in cultured Hep3B cells in the same manner as in Example 1, except that siRNA/RNAiMax mixed solution was prepared with a final concentration of 0.003 to 10 nM double-stranded nucleic acid and 0.3% RNAiMax. As in Example 1, the C5 mRNA expression level in the case of Lipofection only was defined as 100%, and a C5 mRNA residual rate (relative value) was calculated for each introduction of siRNA. The results are shown in Table 11.

| Double strand ID | Numbers of nucleotides in sense strand/antisense strand | Sense strand Sequence (5'→3') | SEQ ID NO |
| --- | --- | --- | --- |
| siRNA-008-01 | 21/21 | uGGuAuAuGuGuuGcuGAuuu | 159 |
| siRNA-008-31 | 19/23 | uGGuAuAuGuGuuGcuGAu | 139 |
| siRNA-008-33 | 19/23 | uGGuAuAuGuGuuGCuGAu | 143 |
| siRNA-008-34 | 19/23 | uGGuAuAuGuGuuGCuGAu | 145 |
| siRNA-008-35 | 19/23 | uGGuAuAuGuGuuGCuGAu | 147 |
| Mock | 21/21 | cuuAcGcuGAGuAcuucGAdT+dT | 87 |

| Double strand ID | Antisense strand Sequence (5'→3') | SEQ ID NO |
| --- | --- | --- |
| siRNA-008-01 | AUcAGcAAcAcAuACcAuu | 160 |
| siRNA-008-31 | AUcAGcAAcAcAuAuACcAuuuu | 140 |
| siRNA-008-33 | AUcAGcAAcAcAuAuACcAuuaa | 144 |
| siRNA-008-34 | AUcAGcAAcAcAuAuACcAuu+a+a | 146 |
| siRNA-008-35 | AUcAGcAAcAcAuAuACcA+u+uaa | 148 |
| Mock | UCGAAGuACUcAGCGuaAAGdT+dT | 88 |

TABLE 11

| siRNA (nM) | Double strand ID | C5 mRNA residual rate (n = 3, average) |
| --- | --- | --- |
| 10 | siRNA-008-01 | 17% |
| 3 | siRNA-008-01 | 20% |
| 1 | siRNA-008-01 | 22% |
| 0.3 | siRNA-008-01 | 26% |
| 0.1 | siRNA-008-01 | 34% |
| 0.03 | siRNA-008-01 | 60% |
| 0.01 | siRNA-008-01 | 66% |
| 0.003 | siRNA-008-01 | 85% |
| 10 | siRNA-008-31 | 16% |
| 3 | siRNA-008-31 | 22% |
| 1 | siRNA-008-31 | 26% |
| 0.3 | siRNA-008-31 | 35% |
| 0.1 | siRNA-008-31 | 49% |
| 0.03 | siRNA-008-31 | 79% |
| 0.01 | siRNA-008-31 | 96% |
| 0.003 | siRNA-008-31 | 83% |
| 10 | siRNA-008-33 | 15% |
| 3 | siRNA-008-33 | 27% |
| 1 | siRNA-008-33 | 37% |
| 0.3 | siRNA-008-33 | 53% |
| 0.1 | siRNA-008-33 | 70% |
| 0.03 | siRNA-008-33 | 96% |
| 0.01 | siRNA-008-33 | 103% |
| 0.003 | siRNA-008-33 | 112% |
| 10 | siRNA-008-34 | 16% |
| 3 | siRNA-008-34 | 28% |
| 1 | siRNA-008-34 | 34% |
| 0.3 | siRNA-008-34 | 38% |
| 0.1 | siRNA-008-34 | 44% |
| 0.03 | siRNA-008-34 | 68% |
| 0.01 | siRNA-008-34 | 76% |
| 0.003 | siRNA-008-34 | 91% |
| 10 | siRNA-008-35 | 15% |
| 3 | siRNA-008-35 | 23% |
| 1 | siRNA-008-35 | 30% |
| 0.3 | siRNA-008-35 | 42% |
| 0.1 | siRNA-008-35 | 59% |
| 0.03 | siRNA-008-35 | 87% |
| 0.01 | siRNA-008-35 | 92% |
| 0.003 | siRNA-008-35 | 98% |
| 10 | Mock | 116% |
| — | Lipofection only | 100% |

Example 5: In-Vivo Screening (Overhang Modification)

(Preparation of siRNA-LNPs)

Lipid nanoparticles (LNPs) encapsulating siRNA therein were prepared in the same manner as in Example 3, except that siRNAs listed in Table 12 were used. Results of evaluation of product quality for the prepared LNPs are shown in Table 13.

TABLE 12

| Double strand ID | Numbers of nucleotides in sense strand/antisense strand | Sense strand Sequence (5'→3') | SEQ ID NO | Antisense strand Sequence (5'→3') | SEQ ID NO |
|---|---|---|---|---|---|
| Mock | 21/21 | cuuAcGcuGAGuAcuucGAdT^dT | 87 | UCGAAGuACUcAGCGuAAGdT^dT | 88 |
| siRNA-008 | 21/21 | uGGuAuAuGuGuuGcuGAudT^dT | 13 | AUcAGcAAcAcAuAuACcAdT^dT | 14 |
| siRNA-008-32 | 19/23 | uGGuAuAuGuGuuGCuGAu | 141 | AUcAGcAAcAcAuAuACcAuuuu | 142 |
| siRNA-008-33 | 19/23 | uGGuAuAuGuGuuGCuGAu | 143 | AUcAGcAAcAcAuAuACcAuuaa | 144 |
| sIRNA-008-34 | 19/23 | uGGuAuAuGuGuuGCuGAu | 145 | AUcAGcAAcAcAuAuACcAuu^a^a | 146 |
| siRNA-008-35 | 19/23 | uGGuAuAuGuGuuGCuGAu | 147 | AUcAGcAAcAcAuAuACcA^u^uaa | 148 |
| sIRNA-008-38 | 19/23 | u^GGuAuAuGuGuuGCuGAu | 153 | AUcAGcAAcAcAuAuACcA^u^uaa | 154 |

TABLE 13

| Double strand ID | Encapsulation efficiency | Average particle size (nm) | Polydispersity index |
|---|---|---|---|
| Mock | >90% | 76 | 0.11 |
| siRNA-008 | >90% | 68 | 0.01 |
| siRNA-008-32 | >90% | 68 | 0.03 |
| siRNA-008-33 | >90% | 69 | 0.05 |
| siRNA-008-34 | >90% | 70 | 0.06 |
| siRNA-008-35 | >90% | 71 | 0.02 |
| siRNA-008-38 | >90% | 70 | 0.01 |

(In-Vivo Screening)

LNPs encapsulating PBS or siRNA listed in Table 12 therein were intravenously administered to a BALB/c mouse (male, 6 weeks old, n=3 per group) from the tail vein at a dose of 0.3 mg/kg siRNA, and the blood and liver were sampled under anesthesia 5 days, 14 days, and 21 days after the administration. From the liver frozen with liquid nitrogen, Total RNA was purified by using an RNeasy Plus Mini Kit (Qiagen, Cat#74106) in accordance with a protocol provided by the manufacturer. Thereafter, cDNA was prepared by using a PrimeScript RT Master Mix (Perfect Real Time) (Takara Bio Inc., Cat#RR036A) in accordance with a protocol provided by the manufacturer. Further, Ct values were measured for the target gene mouse C5 and the endogenous control gene mouse GAPDH by using a TaqMan (registered trademark) Gene Expression Master Mix (Applied Biosystem, Cat#4369510) and a TaqMan probe (Applied Biosystems, C5: Mm01336776_g1; GAPDH: Mm99999915_g1) with an ABI7500 Fast (Applied Biosystems) in accordance with a protocol provided by the manufacturer. The liver C5 mRNA residual rate on each day of measurement for the PBS administration group was defined as 100%, and liver C5 mRNA residual rates (relative values) were calculated for each siRNA administration group by using the comparative Ct method. The results are shown in Table 14.

TABLE 14

| | Liver C5 mRNA residual rate (n = 3, average) | | |
|---|---|---|---|
| Double strand ID | 5 days after administration | 14 days after administration | 21 days after administration |
| PBS | 100% | 100% | 100% |
| Mock | 90% | 119% | 82% |
| siRNA-008 | 22% | 35% | 60% |
| siRNA-008-32 | 22% | 23% | 46% |
| siRNA-008-33 | 17% | 37% | 47% |
| siRNA-008-34 | 16% | 26% | 35% |
| siRNA-008-35 | 12% | 20% | 47% |
| siRNA-008-38 | 14% | 24% | 40% |

The blood sampled on each sampling day was centrifuged at 3000 rpm for 15 minutes, and then the heparin plasma as the supernatant was collected and stored at −80° C. Thereafter, the plasma Mouse C5 was quantified by ELISA. Specifically, the mouse anti-C5 antibody BB5.1 (Hycult Biotech, Cat#HM1073-FS) as an immobilized antibody was diluted with PBS(−) (Wako Pure Chemical Industries, Ltd., #045-29795) to a final concentration of 2 μg/mL and added to an assay plate (Nunc, Cat#442404), and incubated at 4° C. overnight. Thereafter, blocking solution (PBS(−) (Wako Pure Chemical Industries, Ltd.) containing 1% BSA (R&D systems, Inc., Cat#DY995)) was added, and the resultant was incubated at room temperature for 1 hour. The blocking solution was discarded, and washing was performed three times with washing solution (PBS(−) (Wako Pure Chemical Industries, Ltd.) containing 0.02% Tween20). The washing solution was discarded, and the heparin plasma sample diluted with blocking solution was then added, and the resultant was incubated at room temperature for 5 hours. The plasma of the PBS administration group was used as a standard sample. The sample was discarded, and washing was then performed five times with washing solution, and a goat anti-human C5 antibody (Quidel Corporation, Cat#A306) diluted 4000-fold with blocking solution was added, and the resultant was incubated at room temperature for 1 hour. The antibody was discarded, and washing was then performed five times with washing solution, and an HRP-labeled donkey anti-goat IgG (H+L) (Jackson ImmunoResearch Inc., Cat#805-035-180) diluted 40000-fold with blocking solution was added, and the resultant was incubated at room temperature for 1 hour. The antibody was discarded, and washing was then performed five times with washing solution. Thereafter, equal amounts of TMB (3,3′,5,5′-tetramethylbenzidine) Peroxidase Substrate (Kirkegaard & Perry Laboratories, Inc., Cat#50-76-01) and Peroxidase Substrate Solution B (Kirkegaard & Perry Laboratories, Inc., Cat#50-65-00) were mixed together as detection reagent, which was added and allowed to develop color. $H_2SO_4$ (Wako Pure Chemical Industries, Ltd., Cat#198-09595) was added as quenching solution, and absorbance was then measured at 450 nm and 650 nm. Relative values for the samples as the plasma C5 concentration on the day before the administration for the PBS administration group was defined as 100%, are shown in Table 15.

TABLE 15

| | Plasma C5 residual rate (n = 3, average) | | |
|---|---|---|---|
| Double strand ID | 5 days after administration | 14 days after administration | 21 days after administration |
| PBS | 98% | 97% | 101% |
| Mock | 106% | 104% | 108% |
| siRNA-008 | 8% | 21% | 47% |
| siRNA-008-32 | 9% | 15% | 42% |
| siRNA-008-33 | 7% | 29% | 50% |
| siRNA-008-34 | 4% | 11% | 29% |
| siRNA-008-35 | 7% | 19% | 49% |
| siRNA-008-38 | 5% | 17% | 42% |

Figure 2:
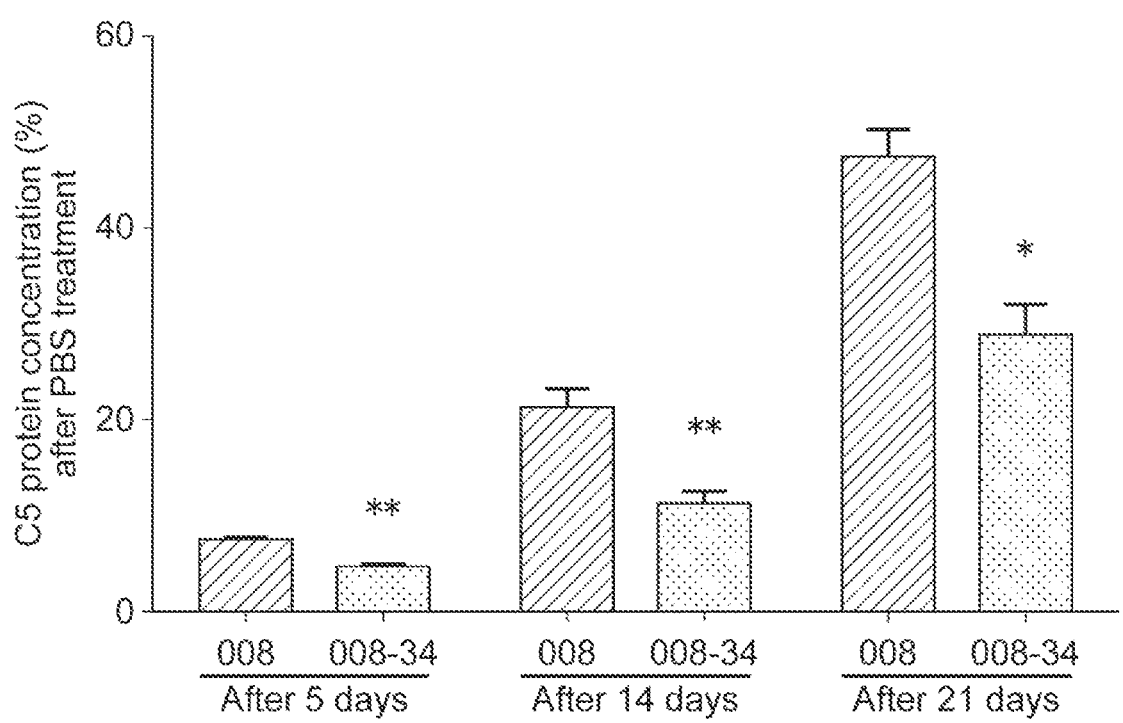
FIG. 2 shows graphs representing results of plasma C5 residual rates after administration of siRNA-008 and plasma C5 residual rates after administration of siRNA-008-34 in Example 5.

Liver C5 mRNA residual rates and plasma C5 concentrations 5 days, 14 days, and 21 days after the administration were quantified, and subjected to statistical analysis (unpaired T-test) for the siRNA-008-34 administration group to the siRNA-008 administration group. The results are shown in FIG. 1 and FIG. 2. Groups with a P value of 0.05 or lower were provided with * (asterisk), and groups with a P value of 0.01 or lower were provided with **.

Example 6: In-Vitro Analysis (Sequence Walk)

Sense strands and antisense strands listed in Table 16 were synthesized by using the phosphoramidite method, and then annealed to synthesize double-stranded nucleic acids (GeneDesign, Inc.). As in Example 1, the C5 mRNA expression level in the case of Lipofection only was defined as 100%, and a C5 mRNA residual rate (relative value) was calculated for each introduction of siRNA. The results are shown in Table 17.

TABLE 16

| Double strand ID | Numbers of nucleotides in sense strand/ antisense strand | Sense strand Sequence (5'→3') | SEQ ID NO | Antisense strand Sequence (5'→3') | SEQ ID NO | Target site in NM_001735.2 |
|---|---|---|---|---|---|---|
| Seq2449 | 21/21 | AcuGGuAuAuGuGuuGcuDdT^dT | 165 | cAGcAAcAcAuAuACcAGUdT^dT | 166 | 2449-2467 |
| Seq2450 | 21/21 | cuGGuAuAuGuGuuGcuGAdT^dT | 167 | UcAGcAAcAcAuAuACcAGdT^dT | 168 | 2450-2468 |
| Seq2451 (=siRNA-008) | 21/21 | uGGuAuAuGuGuuGcuGAudT^dT | 13 | AUcAGcAAcAcAuAuACcAdT^dT | 14 | 2451-2469 |
| Seq2452 | 21/21 | GGuAuAuGuGuuGcuGAuAdT^dT | 169 | uAUcAGcAAcAcAuAuACCdT^dT | 170 | 2452-2470 |
| Seq2453 | 21/21 | GuAuAuGuGuuGcuGAuAcdT^dT | 171 | GuAUcAGcAAcAcAuAuACdT^dT | 172 | 2453-2471 |
| Mock | 21/21 | cuuAcGcuGAGuAcuucGAdT^dT | 87 | UCGAAGuACUcAGCGuAAGdT^dT | 88 | — |

TABLE 17

| siRNA (nM) | Double strand ID | C5 mRNA residual rate (n = 3, average) |
|---|---|---|
| 10 nM | Seq2449 | 107% |
| | Seq2450 | 105% |
| | Seq2451 (=siRNA-008) | 12% |
| | Seq2452 | 111% |
| | Seq2453 | 20% |
| 1 nM | Seq2449 | 110% |
| | Seq2450 | 97% |
| | Seq2451 (=siRNA-008) | 14% |
| | Seq2452 | 107% |
| | Seq2453 | 24% |
| 10 nM | Mock | 96% |
| — | Lipofection only | 100% |

Example 7: Pharmacological Test (Hemolysis-Suppressing Effect)

(Preparation of siRNA-LNPs)
Lipid nanoparticles (LNPs) encapsulating siRNA therein were prepared in the same manner as in Example 3, except that siRNAs listed in Table 18 were used. Results of evaluation of product quality for the prepared LNPs are shown in Table 19.

TABLE 18

| Double strand ID | Numbers of nucleotides in sense strand/antisense strand | Sense strand Sequence (5'→3') | SEQ ID NO | Antisense strand Sequence (5'→3') | SEQ ID NO |
|---|---|---|---|---|---|
| Mock | 21/21 | cuuAcGcuGAGuAcuucGAdT^dT | 89 | UCGAAGuACUcAGCGuAAGdT^dT | 90 |
| siRNA-008-34 | 19/23 | uGGuAuAuGuGuuGCuGAu | 145 | AUcAGcAAcAcAuAuACcAuu^a^a | 146 |

TABLE 19

| Double strand ID | Encapsulation efficiency | Average particle size (nm) | Polydispersity index |
|---|---|---|---|
| Mock | >90% | 92 | 0.06 |
| siRNA-008-34 | >90% | 88 | 0.1 |

(In-Vivo Evaluation)

LNPs encapsulating PBS or siRNA listed in Table 18 therein were intravenously administered to a BALB/c mouse (male, 6 weeks old, n=3 per group) from the tail vein at a dose of 1 to 3 mg/kg siRNA, and the blood was sampled under anesthesia 5 days and 9 days after the administration. The blood sampled on each sampling day was placed in a blood separator tube containing clot activator (Immuno-Biological Laboratories Co, Ltd., Cat#31203) and centrifuged at 3000 rpm for 15 minutes, and then the serum as the supernatant was collected and stored at −80° C. Thereafter, the complement activity in the serum was quantified in the following manner. Specifically, sheep erythrocytes with a concentration of 1.5×10⁸ cells/mL were prepared by using a serum complement titer CH50 kit (DENKA SEIKEN Co., Ltd., Cat#400017) in accordance with a protocol provided by the manufacturer. Subsequently, zymosan (Wako Pure Chemical Industries, Ltd., Cat#263-01491) was prepared so as at a dose of 20 μg/mL with a diluting medium attached to the serum complement titer CH50 kit. The sample serum was diluted 40-fold with the same diluting medium. The sheep erythrocytes, the zymosan, and the diluted serum sample each in a volume of 50 μL were mixed together, and the mixture was incubated at 37° C. overnight. On the next day, the assay plate was centrifuged at 2000 rpm at room temperature for 10 minutes, and the absorbance of the supernatant was then measured at 405 nm. Values for the samples as the complement activity in the serum on the day before the administration to each individual was defined as 100% are shown in Table 20.

TABLE 20

| Double strand ID | siRNA (mg/kg) | Complement activity (n = 3, average) 5 days after administiation | 9 days after administialion |
|---|---|---|---|
| PBS | — | 106% | Not tested |
| Mock | 1 | 130% | 126% |

TABLE 20-continued

| Double strand ID | siRNA (mg/kg) | Complement activity (n = 3, average) 5 days after administiation | 9 days after administialion |
|---|---|---|---|
| siRNA-008-34 | 1 | 2% | 6% |
| siRNA-008-34 | 3 | 2% | 0% |

Example 8: Pharmacological Test
(Hemolysis-Suppressing Effect with Single Administration)

(Preparation of siRNA-LNPs)

Lipid nanoparticles (LNPs) encapsulating siRNA therein were prepared in the same manner as in Example 3, except that siRNAs listed in Table 21 were used. Results of evaluation of product quality for the prepared LNPs are shown in Table 22.

TABLE 21

| Double strand ID | Numbers of nucleotides in sense strand/antisense strand | Sense strand Sequence (5'→3') | SEQ ID NO | Antisense strand Sequence (5'→3') | SEQ ID NO |
|---|---|---|---|---|---|
| siRNA-008-34 | 19/23 | uGGuAuAuGuGuuGCuGAu | 145 | AUcAGcAAcAcAuAuACcAuu^a^a | 146 |

TABLE 22

| Double strand ID | Encapsulation efficiency | Average particle size (nm) | Polydispersity index |
|---|---|---|---|
| siRNA-008-34 | >90% | 92 | 0.09 |

(In-Vivo Evaluation)

Figure 3:
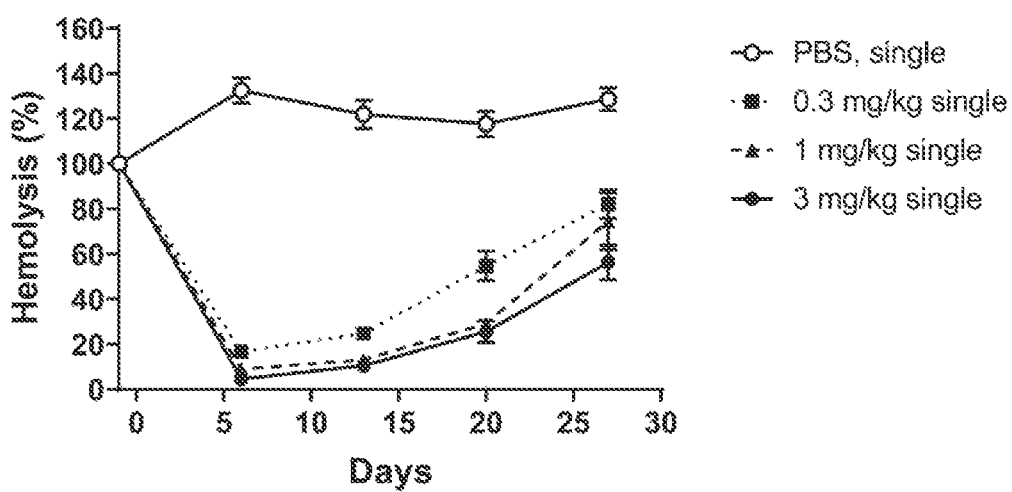
FIG. 3 shows graphs representing results of complement activity after administration of siRNA-008-34 in Example 8.

LNPs encapsulating PBS or siRNA listed in Table 21 therein were intravenously administered to a BALB/c mouse (male, 7 weeks old, n=4 per group) from the tail vein at a dose of 0.3, 1 and 3 mg/kg siRNA, and the blood was sampled under anesthesia on the day before the administration (−1 Day in Table 23), and 6 days, 13 days, 20 days and 27 days after the administration (6 Day, 13 Day, 20 Day and 27 Day in Table 23). The blood sampled on each sampling day was placed in a blood separator tube containing clot activator (Immuno-Biological Laboratories Co, Ltd., Cat#31203) and centrifuged at 3000 rpm for 15 minutes, and then the serum as the supernatant was collected and stored at −80° C. Thereafter, the complement activity in the serum was quantified in the following manner. Specifically, sheep erythrocytes with a concentration of 1.5×10⁸ cells/mL were prepared by using a serum complement titer CH50 kit (DENKA SEIKEN Co., Ltd., Cat#400017) in accordance with a protocol provided by the manufacturer. Subsequently, zymosan (Wako Pure Chemical Industries, Ltd., Cat#263-01491) was prepared so as at a dose of 20 µg/mL with a diluting medium attached to the serum complement titer CH50 kit. The sample serum was diluted 40-fold with the same diluting medium. The sheep erythrocytes, the zymosan, and the diluted serum sample each in a volume of 50 µL were mixed together, and the mixture was incubated at 37° C. overnight. On the next day, the assay plate was centrifuged at 2000 rpm at room temperature for 10 minutes, and the absorbance of the supernatant was then measured at 405 nm. Values for the samples as the complement activity in the serum on the day before the administration (−1 Day in Table 23) to each individual was defined as 100% are shown in Table 23. Complement activity from 1 mouse in 1 mg/kg group was excluded because it was seemed to be outlier. Therefore, only the value of 1 mg/kg group in Table 23 is shown as the average of 3 mice. The values of PBS group, 0.3 mg/kg group and 3 mg/kg group in Table 23 are shown as the average of 4 mice. The results are also shown in FIG. 3.

TABLE 23

| siRNA | | Complement activity (average) | | | | |
|---|---|---|---|---|---|---|
| Double strand ID | (mg/kg) | −1 Day | 6 Day | 13 Day | 20 Day | 27 Day |
| PBS | — | 100% | 133% | 122% | 118% | 129% |
| siRNA-008-34 | 0.3 | 100% | 17% | 25% | 55% | 82% |
| siRNA-008-34 | 1 | 100% | 9% | 13% | 29% | 75% |
| siRNA-008-34 | 3 | 100% | 5% | 10% | 26% | 56% |

Example 9: Pharmacological Test
(Hemolysis-Suppressing Effect with Bi-Weekly Administration)

(Preparation of siRNA-LNPs)

Lipid nanoparticles (LNPs) encapsulating siRNA therein were prepared in the same manner as in Example 8.

(In-Vivo Evaluation)

Figure 4:
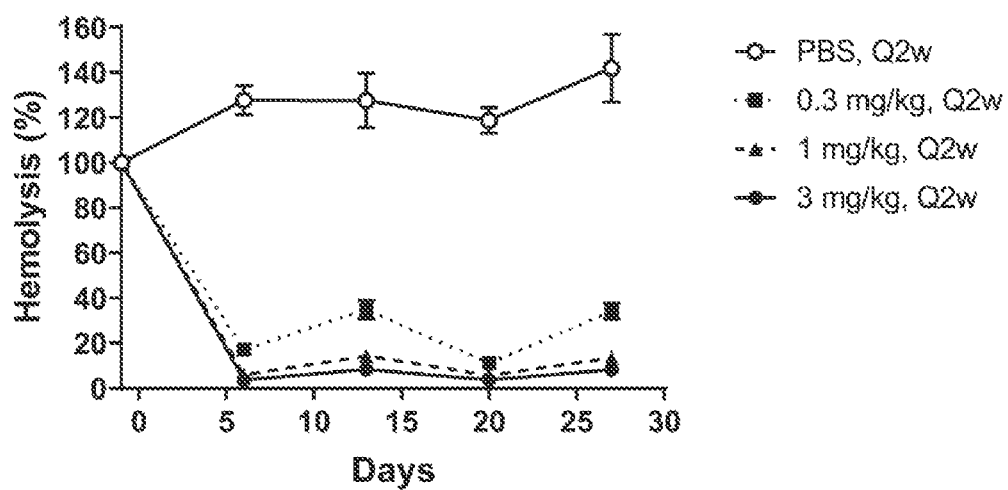
FIG. 4 shows graphs representing results of complement activity after administration of siRNA-008-34 in Example 9.

LNPs encapsulating PBS or siRNA listed in Table 21 of Example 8 therein were intravenously administered to a BALB/c mouse (male, 7 weeks old, n=4 per group) from the tail vein at a dose of 0.3, 1 and 3 mg/kg siRNA bi-weekly (Q2w). The blood was sampled under anesthesia on the day before the administration (−1 Day in Table 24), and 6 days, 13 days, 20 days and 27 days after the administration (6 Day, 13 Day, 20 Day and 27 Day in Table 24). The blood sampled on each sampling day was placed in a blood separator tube containing clot activator (Immuno-Biological Laboratories Co, Ltd., Cat#31203) and centrifuged at 3000 rpm for 15 minutes, and then the serum as the supernatant was collected and stored at −80° C. Thereafter, the complement activity in the serum was quantified in the following manner. Specifically, sheep erythrocytes with a concentration of $1.5 \times 10^8$ cells/mL were prepared by using a serum complement titer CH50 kit (DENKA SEIKEN Co., Ltd., Cat#400017) in accordance with a protocol provided by the manufacturer. Subsequently, zymosan (Wako Pure Chemical Industries, Ltd., Cat#263-01491) was prepared so as at a dose of 20 µg/mL with a diluting medium attached to the serum complement titer CH50 kit. The sample serum was diluted 40-fold with the same diluting medium. The sheep erythrocytes, the zymosan, and the diluted serum sample each in a volume of 50 µL were mixed together, and the mixture was incubated at 37° C. overnight. On the next day, the assay plate was centrifuged at 2000 rpm at room temperature for 10 minutes, and the absorbance of the supernatant was then measured at 405 nm. Values for the samples as the complement activity in the serum on the day before the administration (−1 Day in Table 24) to each individual was defined as 100% are shown in Table 24. The results are also shown in FIG. 4.

TABLE 24

| siRNA | | Complement activity (n = 4, average) | | | | |
|---|---|---|---|---|---|---|
| Double strand ID | (mg/kg) | −1 Day | 6 Day | 13 Day | 20 Day | 27 Day |
| PBS | — | 100% | 128% | 128% | 119% | 142% |
| siRNA-008-34 | 0.3 | 100% | 17% | 35% | 11% | 34% |
| siRNA-008-34 | 1 | 100% | 6% | 14% | 6% | 13% |
| siRNA-008-34 | 3 | 100% | 4% | 8% | 4% | 8% |

Example 10: Pharmacological Test
(Hemolysis-Suppressing Effect with Bi-Weekly Administration)

(Preparation of siRNA-LNPs)

Lipid nanoparticles (LNPs) encapsulating siRNA therein were prepared in the same manner as in Example 8.

(In-Vivo Evaluation)

Figure 5:
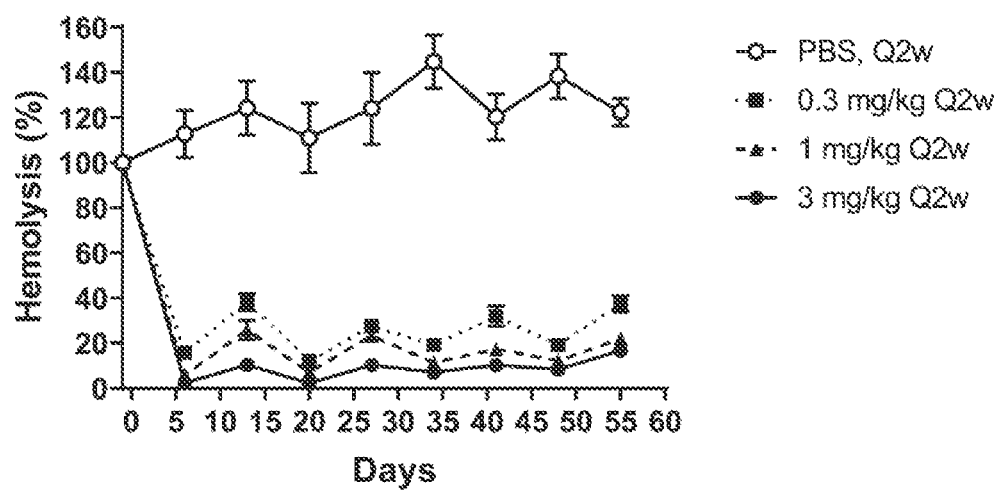
FIG. 5 shows graphs representing results of complement activity after administration of siRNA-008-34 in Example 10.

LNPs encapsulating PBS or siRNA listed in Table 21 of Example 8 therein were intravenously administered to a BALB/c mouse (male, 7 weeks old, n=4 per group) from the tail vein at a dose of 0.3, 1 and 3 mg/kg siRNA bi-weekly (Q2w). The blood was sampled under anesthesia on the day before the administration (−1 Day in Table 25), and 6 days, 13 days, 20 days, 27 days, 34 days, 41 days, 48 days and 55 days after the administration (6 Day, 13 Day, 20 Day, 27 Day, 34 Day, 41 Day, 48 Day and 55 Day in Table 25). The blood sampled on each sampling day was placed in a blood separator tube containing clot activator (Immuno-Biological Laboratories Co, Ltd., Cat#31203) and centrifuged at 3000 rpm for 15 minutes, and then the serum as the supernatant was collected and stored at −80° C. Thereafter, the complement activity in the serum was quantified in the following manner. Specifically, sheep erythrocytes with a concentration of $1.5 \times 10^8$ cells/mL were prepared by using a serum complement titer CH50 kit (DENKA SEIKEN Co., Ltd., Cat#400017) in accordance with a protocol provided by the manufacturer. Subsequently, zymosan (Wako Pure Chemical Industries, Ltd., Cat#263-01491) was prepared so as at a dose of 20 µg/mL with a diluting medium attached to the serum complement titer CH50 kit. The sample serum was diluted 40-fold with the same diluting medium. The sheep erythrocytes, the zymosan, and the diluted serum sample each in a volume of 50 µL were mixed together, and the mixture was incubated at 37° C. overnight. On the next day, the assay plate was centrifuged at 2000 rpm at room temperature for 10 minutes, and the absorbance of the supernatant was then measured at 405 nm. Values for the samples as the complement activity in the serum on the day before the administration (−1 Day in Table 25) to each individual was defined as 100% are shown in Table 25. The results are also shown in FIG. 5.

TABLE 25

| | siRNA | Complement activity (n = 4, average) | | | | | | | | |
|---|---|---|---|---|---|---|---|---|---|---|
| Double strand ID | (mg/kg) | −1 Day | 6 Day | 13 Day | 20 Day | 27 Day | 34 Day | 41 Day | 48 Day | 51 Day |
| PBS | — | 100% | 113% | 124% | 111% | 124% | 145% | 120% | 138% | 122% |
| siRNA-008-34 | 0.3 | 100% | 16% | 38% | 12% | 27% | 19% | 32% | 19% | 37% |
| siRNA-008-34 | 1 | 100% | 6% | 26% | 7% | 23% | 11% | 17% | 12% | 22% |
| siRNA-008-34 | 3 | 100% | 2% | 10% | 2% | 10% | 7% | 10% | 8% | 17% |

Example 11: Pharmacological Test
(Hemolysis-Suppressing Effect with Administration Once Every Three Weeks)

(Preparation of siRNA-LNPs)

Lipid nanoparticles (LNPs) encapsulating siRNA therein were prepared in the same manner as in Example 8.

(In-Vivo Evaluation)

Figure 6:
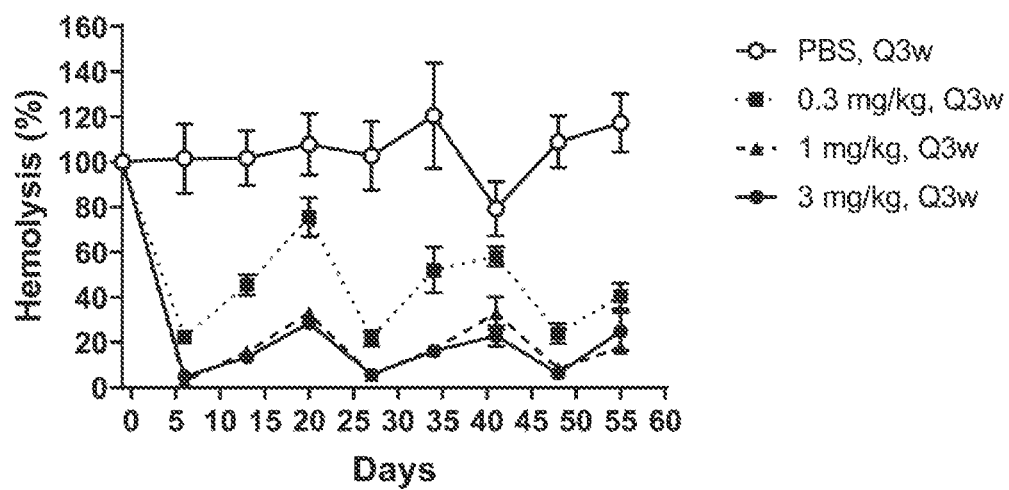
FIG. 6 shows graphs representing results of complement activity after administration of siRNA-008-34 in Example 11.

LNPs encapsulating PBS or siRNA listed in Table 21 of Example 8 therein were intravenously administered to a BALB/c mouse (male, 7 weeks old, n=4 per group) from the tail vein at a dose of 0.3, 1 and 3 mg/kg siRNA once every three weeks (Q3w). The blood was sampled under anesthesia on the day before the administration (−1 Day in Table 26), and 6 days, 13 days, 20 days, 27 days, 34 days, 41 days, 48 days and 55 days after the administration (6 Day, 13 Day, 20 Day, 27 Day, 34 Day, 41 Day, 48 Day and 55 Day in Table 26). The blood sampled on each sampling day was placed in a blood separator tube containing clot activator (Immuno-Biological Laboratories Co., Ltd., Cat#31203) and centrifuged at 3000 rpm for 15 minutes, and then the serum as the supernatant was collected and stored at −80° C. Thereafter, the complement activity in the serum was quantified in the following manner. Specifically, sheep erythrocytes with a concentration of $1.5 \times 10^8$ cells/mL were prepared by using a serum complement titer CH50 kit (DENKA SEIKEN Co., Ltd., Cat#400017) in accordance with a protocol provided by the manufacturer. Subsequently, zymosan (Wako Pure Chemical Industries, Ltd., Cat#263-01491) was prepared so as at a dose of 20 μg/mL with a diluting medium attached to the serum complement titer CH50 kit. The sample serum was diluted 40-fold with the same diluting medium. The sheep erythrocytes, the zymosan, and the diluted serum sample each in a volume of 50 μL were mixed together, and the mixture was incubated at 37° C. overnight. On the next day, the assay plate was centrifuged at 2000 rpm at room temperature for 10 minutes, and the absorbance of the supernatant was then measured at 405 nm. Values for the samples as the complement activity in the serum on the day before the administration (−1 Day in Table 26) to each individual was defined as 100% are shown in Table 26. The results are also shown in FIG. 6.

TABLE 26

| | siRNA | Complement activity (n = 4, average) | | | | | | | | |
|---|---|---|---|---|---|---|---|---|---|---|
| Double strand ID | (mg/kg) | −1 Day | 6 Day | 13 Day | 20 Day | 27 Day | 34 Day | 41 Day | 48 Day | 51 Day |
| PBS | — | 100% | 102% | 102% | 108% | 103% | 120% | 79% | 109% | 117% |
| siRNA-008-34 | 0.3 | 100% | 22% | 45% | 75% | 22% | 52% | 58% | 24% | 40% |
| siRNA-008-34 | 1 | 100% | 3% | 16% | 33% | 6% | 17% | 33% | 8% | 18% |
| siRNA-008-34 | 3 | 100% | 5% | 13% | 29% | 6% | 16% | 23% | 6% | 25% |

What is claimed is:

1. A double-stranded ribonucleic acid comprising:
a combination of a sense strand and an antisense strand, wherein the combination of the sense strand and the antisense strand are selected from the group consisting of combinations:
SEQ ID NO: 159 and SEQ ID NO: 160; SEQ ID NO: 141 and SEQ ID NO: 142; SEQ ID NO: 143 and SEQ ID NO: 144; SEQ ID NO: 145 and SEQ ID NO: 146; SEQ ID NO: 147 and SEQ ID NO: 148; and SEQ ID NO: 153 and SEQ ID NO: 154.

2. A double-stranded ribonucleic acid comprising a sense strand of SEQ ID NO: 159; and an antisense strand of SEQ ID NO: 160.

3. A double-stranded ribonucleic acid comprising a sense strand of SEQ ID NO: 145; and an antisense strand of SEQ ID NO: 146.

4. A double-stranded ribonucleic acid comprising a sense strand of SEQ ID NO: 153; and an antisense strand of SEQ ID NO: 154.

5. A lipid complex encapsulating the double-stranded ribonucleic acid according to claim 1.

6. The lipid complex according to claim 5, comprising:
a cationic lipid; and
at least one lipid selected from the group consisting of neutral lipid, polyethylene glycol-modified lipid, and sterol.

7. The lipid complex according to claim 6, wherein the cationic lipid is 2-{9-oxo-9-[(3-pentyloctyl)oxy]nonyl}dodecyl 1-methylpiperidine-4-carboxylate.

8. A lipid complex encapsulating the double-stranded ribonucleic acid according to claim 3.

9. The lipid complex according to claim 8, comprising:
a cationic lipid; and
at least one lipid selected from the group consisting of neutral lipid, polyethylene glycol-modified lipid, and sterol.

10. The lipid complex according to claim 9, wherein the cationic lipid is 2-{9-oxo-9-[(3-pentyloctyl)oxy]nonyl}dodecyl 1-methylpiperidine-4-carboxylate.

11. A pharmaceutical composition comprising:
the double-stranded ribonucleic acid according to claim 1 and a pharmaceutically acceptable carrier.

12. A pharmaceutical composition comprising:
the double-stranded ribonucleic acid according to claim 2 and a pharmaceutically acceptable carrier.

13. A pharmaceutical composition comprising:
the double-stranded ribonucleic acid according to claim 3 and a pharmaceutically acceptable carrier.

14. A pharmaceutical composition comprising:
the double-stranded ribonucleic acid according to claim 4 and a pharmaceutically acceptable carrier.

15. A pharmaceutical composition comprising:
the lipid complex according to claim 5 and a pharmaceutically acceptable carrier.

16. A pharmaceutical composition comprising:
the lipid complex according to claim 8 and a pharmaceutically acceptable carrier.

17. A method for treating paroxysmal nocturnal hemoglobinuria, comprising:
administering the pharmaceutical composition according to claim 13 to a patient in need thereof.

18. A method for treating atypical hemolytic uremic syndrome, comprising:
administering the pharmaceutical composition according to claim 13 to a patient in need thereof.

19. A method for treating paroxysmal nocturnal hemoglobinuria, comprising:
administering the pharmaceutical composition according to claim 16 to a patient in need thereof.

20. A method for treating atypical hemolytic uremic syndrome, comprising:
administering the pharmaceutical composition according to claim 16 to a patient in need thereof.

* * * * *

UNITED STATES PATENT AND TRADEMARK OFFICE
CERTIFICATE OF CORRECTION

PATENT NO. : 10,526,603 B1
APPLICATION NO. : 16/354916
DATED : January 7, 2020
INVENTOR(S) : Yuta Suzuki et al.

It is certified that error appears in the above-identified patent and that said Letters Patent is hereby corrected as shown below:

In the Specification

Column 1
Line 33, delete "CSaR" and insert -- C5aR --.

Column 10
Lines 22-23, delete "2-(9-oxo-9-[(3-pentyloctyl)oxy]nonyl) dodecyl 1-methylpiperidine-4-carboxylate" and insert -- 2-{9-oxo-9-[(3-pentyloctyl)oxy]nonyl}dodecyl 1-methylpiperidine-4-carboxylate --.
Line 49, delete "palmnitoyloleoylphosphatidylcholine" and insert
-- palmitoyloleoylphosphatidylcholine --.

Column 11
Line 11, delete "[(co-" and insert -- [(ω- --.
Line 17, delete "disteaiyloxypropyl." and insert -- distearyloxypropyl. --.

Column 14
Line 14, after "thereof" insert -- . --.

Columns 21-22, Table 4
Line 30, for the SEQ ID NO of the sense strand for siRNA-001-10, delete "98" and insert -- 97 --.

Column 26, Table 8
Line 5, delete "5 days after administiation" and insert -- 5 days after administration --.

Column 27
Line 35, after "11.", insert -- TABLE 10 --.

Columns 27-28
Line 46, delete "dT+dT" and insert -- dT^dT --.

Signed and Sealed this
Twenty-fourth Day of March, 2020

Andrei Iancu
*Director of the United States Patent and Trademark Office*

Line 52, delete "u+a+a" and insert -- uˆaˆa --.
Line 53, delete "A+u+u" and insert -- Aˆuˆu --.
Line 54, delete "dT+dT" and insert -- dTˆdT --.

Column 31, Table 15
Line 53, delete "21 days after admimistration" and insert -- 21 days after administration --.

Column 33, Table 20
Line 64, delete "5 days after administiation" and insert -- 5 days after administration --.
Line 64, delete "9 days after administialion" and insert -- 9 days after administration --.

Column 34, Table 20
Line 17, delete "5 days after administiation" and insert -- 5 days after administration --.
Line 17, delete "9 days after administialion" and insert -- 9 days after administration --.

Column 37, Table 25
Line 4, delete "51 Day" and insert -- 55 Day --.

Column 38, Table 26
Line 37, delete "51 Day" and insert -- 55 Day --.

SEQUENCE LISTING

```
<160> NUMBER OF SEQ ID NOS: 172

<210> SEQ ID NO 1
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
```

-continued

```
<222> LOCATION: (14)..(14)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 1
aggcaaaggu guucaaagan n                                      21

<210> SEQ ID NO 2
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 2
ucuuugaaca ccuuugccun n                                      21

<210> SEQ ID NO 3
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (6)..(7)
<223> OTHER INFORMATION: um
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (11)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
```

```
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 3
cugucuuaac uuucauagan n                                        21

<210> SEQ ID NO 4
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 4
ucuaugaaag uuaagacagn n                                        21

<210> SEQ ID NO 5
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(11)
<223> OTHER INFORMATION: cm
<220> FEATURE:
<221> NAME/KEY: misc_feature
<222> LOCATION: (14)..(14)
<223> OTHER INFORMATION: cm
```

```
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 5
uagcaugugc cagcuacaan n                                              21

<210> SEQ ID NO 6
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 6
uuguagcugg cacaugcuan n                                              21

<210> SEQ ID NO 7
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (7)..(8)
```

```
<223> OTHER INFORMATION: um
<220> FEATURE:
<221> NAME/KEY: misc_feature
<222> LOCATION: (13)..(14)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 7
cugugauugg aauuagaaan n                                         21

<210> SEQ ID NO 8
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 8
uuucuaauuc caaucacagn n                                         21

<210> SEQ ID NO 9
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(14)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
```

```
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 9
aaggcaaagg uguucaaagn n                                              21

<210> SEQ ID NO 10
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 10 cuugaacac cuuugccuun n                                               21

<210> SEQ ID NO 11
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (19)..(19)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 11
gaaaggaacu guuuacaacn n                                              21

<210> SEQ ID NO 12
<211> LENGTH: 21
<212> TYPE: RNA
```

```
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 12
guuguaaaca guuccuuucn n                                              21

<210> SEQ ID NO 13
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 13
ugguauaugu guugcugaun n                                              21
```

```
<210> SEQ ID NO 14
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 14
aucagcaaca cauauaccan n                                              21

<210> SEQ ID NO 15
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (7)..(8)
<223> OTHER INFORMATION: um
<220> FEATURE:
<221> NAME/KEY: misc_feature
<222> LOCATION: (11)..(11)
```

```
<223> OTHER INFORMATION: cm
<220> FEATURE:
<221> NAME/KEY: misc_feature
<222> LOCATION: (12)..(14)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 15 acugcuuaa cuuucauagn n                                                21

<210> SEQ ID NO 16
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 16
cuaugaaagu uaagacagun n                                               21

<210> SEQ ID NO 17
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(5)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
```

```
<222> LOCATION: (9)..(9)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (15)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 17
gugccagcua caagcccagn n                                         21

<210> SEQ ID NO 18
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 18
cugggcuugu agcuggcacn n                                         21

<210> SEQ ID NO 19
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(12)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (17)..(17)
<223> OTHER INFORMATION: cm
<220> FEATURE:
```

```
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 19
aaggaacugu uuacaacuan n                                              21

<210> SEQ ID NO 20
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 20
uaguuguaaa caguuccuun n                                              21

<210> SEQ ID NO 21
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (2)..(3)
<223> OTHER INFORMATION: cm
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (12)..(13)
<223> OTHER INFORMATION: um
```

```
<220> FEATURE:
<221> NAME/KEY: misc_feature
<222> LOCATION: (16)..(17)
<223> OTHER INFORMATION: cm
<220> FEATURE:
<221> NAME/KEY: misc_feature
<222> LOCATION: (18)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 21
uccucuggaa auuggccuun n                                              21

<210> SEQ ID NO 22
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 22
aaggccaauu uccagaggan n                                              21

<210> SEQ ID NO 23
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(2)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
```

```
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 23
uugaaaggaa cuguuuacan n                                              21

<210> SEQ ID NO 24
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 24
uguaaacagu uccuuucaan n                                              21

<210> SEQ ID NO 25
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
```

```
<222> LOCATION: (20)..(21)
<223> OTHER INFORMATION: phosphorothioate bond

<400> SEQUENCE: 25
aaaggaacug uuuacaacun n                                              21

<210> SEQ ID NO 26
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 26
aguuguaaac aguuccuuun n                                              21

<210> SEQ ID NO 27
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(11)
<223> OTHER INFORMATION: um
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond
```

-continued

```
<400> SEQUENCE: 27
aggaacuguu uacaacuaun n                                              21

<210> SEQ ID NO 28
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (12)..(12)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 28
auaguuguaa acaguuccun n                                              21

<210> SEQ ID NO 29
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(15)
<223> OTHER INFORMATION: um
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond
```

<400> SEQUENCE: 29
uacacugaag cauuugaugn n                                                    21

<210> SEQ ID NO 30
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 30
caucaaaugc uucaguguan n                                                    21

<210> SEQ ID NO 31
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)

```
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 31
cacugaagca uuugaugcan n                                              21

<210> SEQ ID NO 32
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 32
ugcaucaaau gcuucagugn n                                              21

<210> SEQ ID NO 33
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (9)..(11)
<223> OTHER INFORMATION: um
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (19)..(19)
<223> OTHER INFORMATION: cm
<220> FEATURE:
<221> NAME/KEY: misc_feature
```

<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 33
cugaagcauu ugaugcaacn n                                         21

<210> SEQ ID NO 34
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 34
guugcaucaa augcuucagn n                                         21

<210> SEQ ID NO 35
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(2)
<223> OTHER INFORMATION: um
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (14)..(15)
<223> OTHER INFORMATION: um
<220> FEATURE:

```
<221> NAME/KEY: misc_feature
<222> LOCATION: (16)..(16)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 35
uucugcaacu gaauucgaun n                                              21

<210> SEQ ID NO 36
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 36
aucgaauuca guugcagaan n                                              21

<210> SEQ ID NO 37
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
```

```
<220> FEATURE:
<221> NAME/KEY: misc_feature
<222> LOCATION: (20)..(21)
<223> OTHER INFORMATION: phosphorothioate bond

<400> SEQUENCE: 37
ugaaaggaac uguuuacaan n                                              21

<210> SEQ ID NO 38
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 38
uuguaaacag uuccuuucan n                                              21

<210> SEQ ID NO 39
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (10)..(12)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
```

<223> OTHER INFORMATION: phosphorothioate bond

<400> SEQUENCE: 39
acugaagcau uugaugcaan n                                          21

<210> SEQ ID NO 40
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 40
uugcaucaaa ugcuucagun n                                          21

<210> SEQ ID NO 41
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (13)..(14)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (17)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature

```
<222> LOCATION: (20)..(21)
<223> OTHER INFORMATION: phosphorothioate bond

<400> SEQUENCE: 41
cauacagaca aaccuguuun n                                              21

<210> SEQ ID NO 42
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 42
aaacagguuu gucuguaugn n                                              21

<210> SEQ ID NO 43
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(14)
<223> OTHER INFORMATION: cm
<220> FEATURE:
<221> NAME/KEY: misc_feature
<222> LOCATION: (15)..(17)
<223> OTHER INFORMATION: um
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 43
aaacaacaag uaccuuuaun n                                              21
```

```
<210> SEQ ID NO 44
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 44
auaaagguac uuguuguuun n                                              21

<210> SEQ ID NO 45
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (12)..(13)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (16)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 45
auacagacaa accuguuuan n                                              21

<210> SEQ ID NO 46
<211> LENGTH: 21
<212> TYPE: RNA
<213> ORGANISM: Artificial Sequence
<220> FEATURE:
<223> OTHER INFORMATION: synthesized siRNA antisense sequence
```

```
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 46
uaaacagguu ugucuguaun n                                       21

<210> SEQ ID NO 47
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(12)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 47
gguauaugug uugcugauan n                                       21

<210> SEQ ID NO 48
```

```
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (12)..(12)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 48
uaucagcaac acauauaccn n                                              21

<210> SEQ ID NO 49
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
```

```
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 49
ucagaaaguc ugugaaggan n                                              21

<210> SEQ ID NO 50
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 50
uccuucacag acuuucugan n                                              21

<210> SEQ ID NO 51
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (4)..(5)
<223> OTHER INFORMATION: cm
<220> FEATURE:
<221> NAME/KEY: misc_feature
<222> LOCATION: (9)..(10)
<223> OTHER INFORMATION: cm
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (17)..(17)
<223> OTHER INFORMATION: um
<220> FEATURE:
```

```
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 51
ucuccaggcc aaacugugun n                                        21

<210> SEQ ID NO 52
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 52
acacaguuug gccuggagan n                                        21

<210> SEQ ID NO 53
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(12)
<223> OTHER INFORMATION: cm
<220> FEATURE:
<221> NAME/KEY: misc_feature
<222> LOCATION: (13)..(15)
<223> OTHER INFORMATION: um
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (19)..(19)
<223> OTHER INFORMATION: um
```

<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 53
acaacaagua ccuuuauaun n                                              21

<210> SEQ ID NO 54
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 54
auauaaaggu acuuguugun n                                              21

<210> SEQ ID NO 55
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(11)
<223> OTHER INFORMATION: cm
<220> FEATURE:
<221> NAME/KEY: misc_feature
<222> LOCATION: (12)..(14)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (18)..(19)

```
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 55
caacaaguac cuuuauauun n                                              21

<210> SEQ ID NO 56
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 56
aauauaaagg uacuuguugn n                                              21

<210> SEQ ID NO 57
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (6)..(7)
<223> OTHER INFORMATION: cm
<220> FEATURE:
<221> NAME/KEY: misc_feature
<222> LOCATION: (11)..(12)
<223> OTHER INFORMATION: cm
<220> FEATURE:
<221> NAME/KEY: misc_feature
<222> LOCATION: (16)..(16)
<223> OTHER INFORMATION: cm
<220> FEATURE:
<221> NAME/KEY: misc_feature
```

```
<222> LOCATION: (17)..(17)
<223> OTHER INFORMATION: um
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 57
auucuccagg ccaaacugun n                                            21

<210> SEQ ID NO 58
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 58
acaguuuggc cuggagaaun n                                            21

<210> SEQ ID NO 59
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (8)..(9)
<223> OTHER INFORMATION: cm
<220> FEATURE:
<221> NAME/KEY: misc_feature
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (14)..(15)
<223> OTHER INFORMATION: cm
<220> FEATURE:
<221> NAME/KEY: misc_feature
<222> LOCATION: (19)..(19)
<223> OTHER INFORMATION: um
<220> FEATURE:
```

```
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 59
guggcaacca gcuccaggun n                                              21

<210> SEQ ID NO 60
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 60
accuggagcu gguugccacn n                                              21

<210> SEQ ID NO 61
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 61
aagagacauc ugacuuggan n                                              21
```

```
<210> SEQ ID NO 62
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 62
uccaagucag augucucuun n                                              21

<210> SEQ ID NO 63
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(3)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 63
```
auucugcaac ugaauucgan n                                                    21

<210> SEQ ID NO 64
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 64
ucgaauucag uugcagaaun n                                                    21

<210> SEQ ID NO 65
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(2)
<223> OTHER INFORMATION: um
<220> FEATURE:
<221> NAME/KEY: misc_feature
<222> LOCATION: (3)..(4)
<223> OTHER INFORMATION: cm
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (13)..(14)
<223> OTHER INFORMATION: um
<220> FEATURE:
<221> NAME/KEY: misc_feature
<222> LOCATION: (17)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 65
uuccucugga aauuggccun n                                21

<210> SEQ ID NO 66
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (12)..(12)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 66
aggccaauuu ccagaggaan n                                21

<210> SEQ ID NO 67
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: cm
<220> FEATURE:
<221> NAME/KEY: misc_feature
<222> LOCATION: (14)..(16)
<223> OTHER INFORMATION: um
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 67
aacaacaagu accuuuauan n                                21

<210> SEQ ID NO 68
<211> LENGTH: 21
<212> TYPE: RNA

```
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 68
uauaaaggua cuuguuguun n                                              21

<210> SEQ ID NO 69
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (8)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (15)..(17)
<223> OTHER INFORMATION: cm
<220> FEATURE:
<221> NAME/KEY: misc_feature
<222> LOCATION: (18)..(18)
<223> OTHER INFORMATION: um
```

```
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 69
aauauguccu cucucccuan n                                              21

<210> SEQ ID NO 70
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 70
uagggagaga ggacauauun n                                              21

<210> SEQ ID NO 71
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (12)..(13)
```

```
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 71
acucacuaua auuacuugan n                                              21

<210> SEQ ID NO 72
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 72
ucaaguaauu auagugagun n                                              21

<210> SEQ ID NO 73
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (6)..(6)
<223> OTHER INFORMATION: um
<220> FEATURE:
<221> NAME/KEY: misc_feature
```

```
<222> LOCATION: (7)..(7)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 73
auaacucacu auaauuacun n                                    21

<210> SEQ ID NO 74
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 74
aguaauuaua gugaguuaun n                                    21

<210> SEQ ID NO 75
<211> LENGTH: 21
<212> TYPE: RNA
```

```
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (9)..(10)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (16)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 75
aaauaugucc ucucucccun n                                          21

<210> SEQ ID NO 76
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (20)..(21)
<223> OTHER INFORMATION: n=deoxythymidine
```

```
<220> FEATURE:
<221> NAME/KEY: misc_feature
<222> LOCATION: (20)..(21)
<223> OTHER INFORMATION: phosphorothioate bond

<400> SEQUENCE: 76
agggagagag gacauauuun n                                              21

<210> SEQ ID NO 77
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(11)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 77
aagauauuuu uauaauaaan n                                              21

<210> SEQ ID NO 78
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 78
```
uuuauuauaa aaauaucuun n                                            21

<210> SEQ ID NO 79
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (12)..(12)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 79
aaaauaacuc acuauaaauun n                                           21

<210> SEQ ID NO 80
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature

```
<222> LOCATION: (20)..(21)
<223> OTHER INFORMATION: phosphorothioate bond

<400> SEQUENCE: 80
aauuauagug aguuauuuun n                                              21

<210> SEQ ID NO 81
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (17)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 81
aaauaacuca cuauaauuan n                                              21

<210> SEQ ID NO 82
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: um
<220> FEATURE:
```

```
<221> NAME/KEY: misc_feature
<222> LOCATION: (15)..(15)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 82
uaauuauagu gaguuauuun n                                               21

<210> SEQ ID NO 83
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(5)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 83
guguuaaaau gucugcugun n                                               21

<210> SEQ ID NO 84
<211> LENGTH: 21
<212> TYPE: RNA
<213> ORGANISM: Artificial Sequence
<220> FEATURE:
<223> OTHER INFORMATION: synthesized siRNA antisense sequence
```

```
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 84
acagcagaca uuuuaacacn n                                              21

<210> SEQ ID NO 85
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(11)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 85
aaaauguuuu ugucaaguan n                                              21

<210> SEQ ID NO 86
<211> LENGTH: 21
<212> TYPE: RNA
<213> ORGANISM: Artificial Sequence
<220> FEATURE:
```

-continued

```
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 86
uacuugacaa aaacauuuun n                                          21

<210> SEQ ID NO 87
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (2)..(3)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 87
```
cuuacgcuga guacuucgan n                                              21

<210> SEQ ID NO 88
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 88
ucgaaguacu cagcguaagn n                                              21

<210> SEQ ID NO 89
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 89
aggcaaaggu guucaaagan n                                              21

<210> SEQ ID NO 90
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:

```
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 90
ucuuugaaca ccuuugccun n                                              21

<210> SEQ ID NO 91
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm

<400> SEQUENCE: 91
aggcaaaggu guucaaaga                                                 19

<210> SEQ ID NO 92
<211> LENGTH: 19
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm

<400> SEQUENCE: 92
ucuuugaaca ccuuugccu                                                 19

<210> SEQ ID NO 93
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
```

```
<220> FEATURE:
<221> NAME/KEY: misc_feature
<222> LOCATION: (10)..(21)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm

<400> SEQUENCE: 93
aggcaaaggu guucaaagau u                                              21

<210> SEQ ID NO 94
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 94
ucuuugaaca ccuuugccuu u                                              21

<210> SEQ ID NO 95
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (2)..(3)
<223> OTHER INFORMATION: phosphorothioate bond
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 95
```
aggcaaaggu guucaaagau u                                              21

<210> SEQ ID NO 96
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(3)
<223> OTHER INFORMATION: phosphorothioate bond
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 96
ucuuugaaca ccuuugccuu u                                              21

<210> SEQ ID NO 97
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (19)..(20)
<223> OTHER INFORMATION: phosphorothioate bond
<220> FEATURE:
<221> NAME/KEY: misc_feature
<222> LOCATION: (20)..(21)
<223> OTHER INFORMATION: phosphorothioate bond
<220> FEATURE:
<221> NAME/KEY: misc_feature
<222> LOCATION: (20)..(21)
<223> OTHER INFORMATION: um

<400> SEQUENCE: 97
aggcaaaggu guucaaagau u                                              21

<210> SEQ ID NO 98
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature

```
<222> LOCATION: (1)..(2)
<223> OTHER INFORMATION: phosphorothioate bond
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (19)..(21)
<223> OTHER INFORMATION: phosphorothioate bond
<220> FEATURE:
<221> NAME/KEY: misc_feature
<222> LOCATION: (20)..(21)
<223> OTHER INFORMATION: um

<400> SEQUENCE: 98
ucuuugaaca ccuuugccuu u                                              21

<210> SEQ ID NO 99
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm

<400> SEQUENCE: 99
aggcaaaggu guucaaaga                                                 19

<210> SEQ ID NO 100
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 100
ucuuugaaca ccuuugccuu u                                              21

<210> SEQ ID NO 101
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
```

```
<221> NAME/KEY: misc_feature
<222> LOCATION: (6)..(6)
<223> OTHER INFORMATION: cm
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(15)
<223> OTHER INFORMATION: um
<220> FEATURE:
<221> NAME/KEY: misc_feature
<222> LOCATION: (16)..(16)
<223> OTHER INFORMATION: cm

<400> SEQUENCE: 101
auaggcaaag guguucaaag a                                              21

<210> SEQ ID NO 102
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 102
ucuuugaaca ccuuugccuu u                                              21

<210> SEQ ID NO 103

<400> SEQUENCE: 103

000

<210> SEQ ID NO 104
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 104
ucuuugaaca ccuuugccuu u                                              21

<210> SEQ ID NO 105

<400> SEQUENCE: 105

000

<210> SEQ ID NO 106
<211> LENGTH: 21
<212> TYPE: RNA
<213> ORGANISM: Artificial Sequence
```

```
<220> FEATURE:
<223> OTHER INFORMATION: synthesized siRNA antisense sequence
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 106
cuuugaacac cuuugccuun n                                              21

<210> SEQ ID NO 107
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(14)
<223> OTHER INFORMATION: um
<220> FEATURE:
<221> NAME/KEY: misc_feature
<222> LOCATION: (15)..(15)
<223> OTHER INFORMATION: cm

<400> SEQUENCE: 107
aaggcaaagg uguucaaag                                                 19

<210> SEQ ID NO 108
<211> LENGTH: 19
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (8)..(8)
<223> OTHER INFORMATION: cm

<400> SEQUENCE: 108
cuuugaacac cuuugccuu                                                 19

<210> SEQ ID NO 109
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
```

```
<221> NAME/KEY: misc_feature
<222> LOCATION: (12)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (19)..(19)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 109
gaaaggaacu guuuacaacn n                                              21

<210> SEQ ID NO 110
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 110
guuguaaaca guuccuuucn n                                              21

<210> SEQ ID NO 111
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (13)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (19)..(19)
<223> OTHER INFORMATION: cm
```

-continued

<400> SEQUENCE: 111
gaaaggaacu guuuacaac                                                19

<210> SEQ ID NO 112
<211> LENGTH: 19
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (9)..(9)
<223> OTHER INFORMATION: cm

<400> SEQUENCE: 112
guuguaaaca guuccuuuc                                                19

<210> SEQ ID NO 113
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 113
ugguauaugu guugcugaun n                                              21

<210> SEQ ID NO 114
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 114
aucagcaaca cauauaccan n                                              21

<210> SEQ ID NO 115
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature

```
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 115
ugguauaugu guugcugau                                            19

<210> SEQ ID NO 116
<211> LENGTH: 19
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm

<400> SEQUENCE: 116
aucagcaaca cauauacca                                            19

<210> SEQ ID NO 117
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (4)..(4)
<223> OTHER INFORMATION: um
<220> FEATURE:
```

```
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(21)
<223> OTHER INFORMATION: um

<400> SEQUENCE: 117
ugguauaugu guugcugauu u                                         21

<210> SEQ ID NO 118
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 118
aucagcaaca cauauaccau u                                         21
```

```
<210> SEQ ID NO 119
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(3)
<223> OTHER INFORMATION: phosphorothioate bond
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(21)
<223> OTHER INFORMATION: um

<400> SEQUENCE: 119
ugguauaugu guugcugauu u                                              21

<210> SEQ ID NO 120
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(3)
<223> OTHER INFORMATION: phosphorothioate bond
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
```

```
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 120
aucagcaaca cauauaccau u                                              21

<210> SEQ ID NO 121
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(21)
<223> OTHER INFORMATION: um
<220> FEATURE:
<221> NAME/KEY: misc_feature
<222> LOCATION: (19)..(21)
<223> OTHER INFORMATION: phosphorothioate bond

<400> SEQUENCE: 121
ugguauaugu guugcugauu u                                              21
```

```
<210> SEQ ID NO 122
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(21)
<223> OTHER INFORMATION: phosphorothioate bond
<220> FEATURE:
<221> NAME/KEY: misc_feature
<222> LOCATION: (20)..(21)
<223> OTHER INFORMATION: um

<400> SEQUENCE: 122
aucagcaaca cauauaccau u                                             21

<210> SEQ ID NO 123
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
```

```
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 123
ugguauaugu guugcugau                                              19

<210> SEQ ID NO 124
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 124
aucagcaaca cauauaccau u                                           21

<210> SEQ ID NO 125
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(3)
<223> OTHER INFORMATION: um
<220> FEATURE:
<221> NAME/KEY: misc_feature
<222> LOCATION: (6)..(6)
<223> OTHER INFORMATION: um
```

```
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (21)..(21)
<223> OTHER INFORMATION: um

<400> SEQUENCE: 125
auugguauau guguugcuga u                                              21

<210> SEQ ID NO 126
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 126
aucagcaaca cauauaccau u                                              21

<210> SEQ ID NO 127
```

```
<211> LENGTH: 22
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (3)..(4)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (22)..(22)
<223> OTHER INFORMATION: um

<400> SEQUENCE: 127
uauugguaua uguguugcug au                                              22

<210> SEQ ID NO 128
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
```

```
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 128
aucagcaaca cauauaccau u                                           21

<210> SEQ ID NO 129
<211> LENGTH: 23
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (3)..(4)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (22)..(22)
<223> OTHER INFORMATION: um
<220> FEATURE:
<221> NAME/KEY: misc_feature
<222> LOCATION: (23)..(23)
<223> OTHER INFORMATION: n=Inverted deoxythymidine

<400> SEQUENCE: 129
uauugguaua uguguugcug aun                                         23

<210> SEQ ID NO 130
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
```

```
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 130
aucagcaaca cauauaccau u                                             21

<210> SEQ ID NO 131
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(21)
<223> OTHER INFORMATION: um

<400> SEQUENCE: 131
ugguauaugu guugcugauu u                                             21
```

```
<210> SEQ ID NO 132
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 132
aucagcaaca cauauaccau u                                       21

<210> SEQ ID NO 133
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
```

```
<223> OTHER INFORMATION: cm
<220> FEATURE:
<221> NAME/KEY: misc_feature
<222> LOCATION: (19)..(21)
<223> OTHER INFORMATION: um

<400> SEQUENCE: 133
ugguauaugu guugcugauu u                                               21

<210> SEQ ID NO 134
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 134
aucagcaaca cauauaccau u                                               21

<210> SEQ ID NO 135
<211> LENGTH: 20
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(3)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
```

<222> LOCATION: (12)..(12)
<223> OTHER INFORMATION: um
<220> FEATURE:
<221> NAME/KEY: misc_feature
<222> LOCATION: (14)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (18)..(18)
<223> OTHER INFORMATION: um

<400> SEQUENCE: 135
auugguauau guguugcuga                    20

<210> SEQ ID NO 136
<211> LENGTH: 20
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (19)..(20)
<223> OTHER INFORMATION: um

<400> SEQUENCE: 136
ucagcaacac auauaccauu                    20

<210> SEQ ID NO 137
<211> LENGTH: 20
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: um
<220> FEATURE:

```
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(20)
<223> OTHER INFORMATION: um

<400> SEQUENCE: 137
augguauaug uguugcugau                                           20

<210> SEQ ID NO 138
<211> LENGTH: 20
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(20)
<223> OTHER INFORMATION: um

<400> SEQUENCE: 138
aucagcaaca cauauaccuu                                           20

<210> SEQ ID NO 139
<211> LENGTH: 19
```

```
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 139
ugguauaugu guugcugau                                                  19

<210> SEQ ID NO 140
<211> LENGTH: 23
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
```

```
<223> OTHER INFORMATION: cm
<220> FEATURE:
<221> NAME/KEY: misc_feature
<222> LOCATION: (20)..(23)
<223> OTHER INFORMATION: um

<400> SEQUENCE: 140
aucagcaaca cauauaccau uuu                                              23

<210> SEQ ID NO 141
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 141
ugguauaugu guugcugau                                                   19

<210> SEQ ID NO 142
<211> LENGTH: 23
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
```

```
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(23)
<223> OTHER INFORMATION: um

<400> SEQUENCE: 142
aucagcaaca cauauaccau uuu                                               23

<210> SEQ ID NO 143
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 143
ugguauaugu guugcugau                                                    19

<210> SEQ ID NO 144
<211> LENGTH: 23
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
```

```
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um
<220> FEATURE:
<221> NAME/KEY: misc_feature
<222> LOCATION: (22)..(23)
<223> OTHER INFORMATION: 2'-o-methyladenosine

<400> SEQUENCE: 144
aucagcaaca cauauaccau uaa                                             23

<210> SEQ ID NO 145
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 145
ugguauaugu guugcugau                                                  19

<210> SEQ ID NO 146
<211> LENGTH: 23
```

```
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um
<220> FEATURE:
<221> NAME/KEY: misc_feature
<222> LOCATION: (21)..(23)
<223> OTHER INFORMATION: phosphorothioate bond
<220> FEATURE:
<221> NAME/KEY: misc_feature
<222> LOCATION: (22)..(23)
<223> OTHER INFORMATION: 2'-o-methyladenosine

<400> SEQUENCE: 146
aucagcaaca cauauaccau uaa                                            23

<210> SEQ ID NO 147
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
```

```
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 147
ugguauaugu guugcugau                                               19

<210> SEQ ID NO 148
<211> LENGTH: 23
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(21)
<223> OTHER INFORMATION: phosphorothioate bond
<220> FEATURE:
<221> NAME/KEY: misc_feature
<222> LOCATION: (20)..(21)
<223> OTHER INFORMATION: um
<220> FEATURE:
<221> NAME/KEY: misc_feature
<222> LOCATION: (22)..(23)
<223> OTHER INFORMATION: 2'-o-methyladenosine

<400> SEQUENCE: 148
aucagcaaca cauauaccau uaa                                          23

<210> SEQ ID NO 149
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
```

<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 149
ugguauaugu guugcugau                                                19

<210> SEQ ID NO 150
<211> LENGTH: 23
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: 2'-o-methyladenosine
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(21)
<223> OTHER INFORMATION: phosphorothioate bond
<220> FEATURE:

```
<221> NAME/KEY: misc_feature
<222> LOCATION: (20)..(21)
<223> OTHER INFORMATION: um
<220> FEATURE:
<221> NAME/KEY: misc_feature
<222> LOCATION: (22)..(23)
<223> OTHER INFORMATION: 2'-o-methyladenosine

<400> SEQUENCE: 150
aucagcaaca cauauaccau uaa                                               23

<210> SEQ ID NO 151
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 151
ugguauaugu guugcugau                                                    19

<210> SEQ ID NO 152
<211> LENGTH: 23
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: 2'-o-methyladenosine
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
```

```
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(23)
<223> OTHER INFORMATION: um

<400> SEQUENCE: 152
aucagcaaca cauauaccau uuu                                              23

<210> SEQ ID NO 153
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (1)..(2)
<223> OTHER INFORMATION: phosphorothioate bond
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(19)
<223> OTHER INFORMATION: um

<400> SEQUENCE: 153
ugguauaugu guugcugau                                                   19

<210> SEQ ID NO 154
<211> LENGTH: 23
<212> TYPE: RNA
<213> ORGANISM: Artificial Sequence
<220> FEATURE:
```

```
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(21)
<223> OTHER INFORMATION: phosphorothioate bond
<220> FEATURE:
<221> NAME/KEY: misc_feature
<222> LOCATION: (20)..(21)
<223> OTHER INFORMATION: um
<220> FEATURE:
<221> NAME/KEY: misc_feature
<222> LOCATION: (22)..(23)
<223> OTHER INFORMATION: 2'-o-methyladenosine

<400> SEQUENCE: 154
aucagcaaca cauauaccau uaa                                              23

<210> SEQ ID NO 155
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
```

```
<222> LOCATION: (12)..(12)
<223> OTHER INFORMATION: um
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 155
auaacucacu auaauuacun n                                      21

<210> SEQ ID NO 156
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 156
aguaauuaua gugaguuaun n                                      21

<210> SEQ ID NO 157
<211> LENGTH: 19
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: cm
<220> FEATURE:
```

```
<221> NAME/KEY: misc_feature
<222> LOCATION: (6)..(6)
<223> OTHER INFORMATION: um
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (15)..(16)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: um

<400> SEQUENCE: 157
auaacucacu auaauuacu                                                19

<210> SEQ ID NO 158
<211> LENGTH: 19
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (17)..(17)
<223> OTHER INFORMATION: um

<400> SEQUENCE: 158
aguaauuaua gugaguuau                                                19

<210> SEQ ID NO 159
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: um
```

```
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (15)..(15)
<223> OTHER INFORMATION: cm
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (19)..(21)
<223> OTHER INFORMATION: um

<400> SEQUENCE: 159
ugguauaugu guugcugauu u                                              21

<210> SEQ ID NO 160
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (3)..(3)
<223> OTHER INFORMATION: cm
<220> FEATURE:
<221> NAME/KEY: misc_feature
<222> LOCATION: (6)..(6)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 160
aucagcaaca cauauaccau u                                              21

<210> SEQ ID NO 161
```

```
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(13)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 161
aggcaaaggu guucaaagau u                                            21

<210> SEQ ID NO 162
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 162
ucuuugaaca ccuuugccuu u                                            21

<210> SEQ ID NO 163
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (19)..(19)
<223> OTHER INFORMATION: cm
<220> FEATURE:
<221> NAME/KEY: misc_feature
```

-continued

<222> LOCATION: (20)..(21)
<223> OTHER INFORMATION: um

<400> SEQUENCE: 163
gaaaggaacu guuuacaacu u                                              21

<210> SEQ ID NO 164
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (20)..(21)
<223> OTHER INFORMATION: um

<400> SEQUENCE: 164
guuguaaaca guuccuuucu u                                              21

<210> SEQ ID NO 165
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(10)
<223> OTHER INFORMATION: um
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(15)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:

-continued

<221> NAME/KEY: misc_feature
<222> LOCATION: (20)..(21)
<223> OTHER INFORMATION: phosphorothioate bond

<400> SEQUENCE: 165
acugguauau guguugcugn n                                              21

<210> SEQ ID NO 166
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (9)..(9)
<223> OTHER INFORMATION: cm
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(13)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 166
cagcaacaca uauaccagun n                                              21

<210> SEQ ID NO 167
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (1)..(1)
<223> OTHER INFORMATION: cm
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: um

```
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(11)
<223> OTHER INFORMATION: um
<220> FEATURE:
<221> NAME/KEY: misc_feature
<222> LOCATION: (13)..(14)
<223> OTHER INFORMATION: um
<220> FEATURE:
<221> NAME/KEY: misc_feature
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 167
cugguauaug uguugcugan n                                              21

<210> SEQ ID NO 168
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: cm
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (10)..(10)
<223> OTHER INFORMATION: cm
<220> FEATURE:
<221> NAME/KEY: misc_feature
<222> LOCATION: (12)..(12)
<223> OTHER INFORMATION: um
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (17)..(17)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 168
```
ucagcaacac auauaccagn n                                             21

```
<210> SEQ ID NO 169
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (3)..(3)
<223> OTHER INFORMATION: um
<220> FEATURE:
<221> NAME/KEY: misc_feature
<222> LOCATION: (5)..(5)
<223> OTHER INFORMATION: um
<220> FEATURE:
<221> NAME/KEY: misc_feature
<222> LOCATION: (7)..(7)
<223> OTHER INFORMATION: um
<220> FEATURE:
<221> NAME/KEY: misc_feature
<222> LOCATION: (9)..(9)
<223> OTHER INFORMATION: um
<220> FEATURE:
<221> NAME/KEY: misc_feature
<222> LOCATION: (11)..(12)
<223> OTHER INFORMATION: um
<220> FEATURE:
<221> NAME/KEY: misc_feature
<222> LOCATION: (14)..(14)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (18)..(18)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 169
```
gguauaugug uugcugauan n                                             21

```
<210> SEQ ID NO 170
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (1)..(1)
<223> OTHER INFORMATION: um
<220> FEATURE:
<221> NAME/KEY: misc_feature
<222> LOCATION: (4)..(4)
<223> OTHER INFORMATION: cm
<220> FEATURE:
<221> NAME/KEY: misc_feature
<222> LOCATION: (7)..(7)
<223> OTHER INFORMATION: cm
<220> FEATURE:
<221> NAME/KEY: misc_feature
<222> LOCATION: (10)..(10)
<223> OTHER INFORMATION: cm
<220> FEATURE:
<221> NAME/KEY: misc_feature
```

```
<222> LOCATION: (12)..(12)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (16)..(16)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 170
uaucagcaac acauauaccn n                                          21

<210> SEQ ID NO 171
<211> LENGTH: 21
<212> TYPE: RNA
<213> ORGANISM: Artificial Sequence
<220> FEATURE:
<223> OTHER INFORMATION: synthesized siRNA sense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (4)..(4)
<223> OTHER INFORMATION: um
<220> FEATURE:
<221> NAME/KEY: misc_feature
<222> LOCATION: (6)..(6)
<223> OTHER INFORMATION: um
<220> FEATURE:
<221> NAME/KEY: misc_feature
<222> LOCATION: (8)..(8)
<223> OTHER INFORMATION: um
<220> FEATURE:
<221> NAME/KEY: misc_feature
<222> LOCATION: (10)..(11)
<223> OTHER INFORMATION: um
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: um
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (19)..(19)
<223> OTHER INFORMATION: cm
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond
```

```
<400> SEQUENCE: 171
guauaugugu ugcugauacn n                                              21

<210> SEQ ID NO 172
<211> LENGTH: 21
<212> TYPE: RNA
<213> ORGANISM: Artificial Sequence
<220> FEATURE:
<223> OTHER INFORMATION: synthesized siRNA antisense sequence
<220> FEATURE:
<221> NAME/KEY: misc_feature
<222> LOCATION: (2)..(2)
<223> OTHER INFORMATION: um
<220> FEATURE:
<221> NAME/KEY: misc_feature
<222> LOCATION: (5)..(5)
<223> OTHER INFORMATION: cm
<220> FEATURE:
<221> NAME/KEY: misc_feature
<222> LOCATION: (8)..(8)
<223> OTHER INFORMATION: cm
<220> FEATURE:
<221> NAME/KEY: misc_feature
<222> LOCATION: (11)..(11)
<223> OTHER INFORMATION: cm
<220> FEATURE:
<221> NAME/KEY: misc_feature
<222> LOCATION: (13)..(13)
<223> OTHER INFORMATION: cm
<220> FEATURE:
<221> NAME/KEY: misc_feature
<222> LOCATION: (15)..(15)
<223> OTHER INFORMATION: um
<220> FEATURE:
<221> NAME/KEY: misc_feature
<222> LOCATION: (17)..(17)
<223> OTHER INFORMATION: um
<220> FEATURE:
<221> NAME/KEY: misc_feature
<222> LOCATION: (20)..(21)
<223> OTHER INFORMATION: n=deoxythymidine
<220> FEATURE:
<221> NAME/KEY: misc_feature
<222> LOCATION: (20)..(21)
<223> OTHER INFORMATION: phosphorothioate bond

<400> SEQUENCE: 172
guaucagcaa cacauauacn n                                              21
```